(12) United States Patent
Muzykantov et al.

(10) Patent No.: US 8,333,973 B2
(45) Date of Patent: Dec. 18, 2012

(54) TARGETING RECOMBINANT THERAPEUTICS TO CIRCULATING RED BLOOD CELLS

(75) Inventors: Vladimir R. Muzykantov, Warwick, PA (US); Sergei V. Zaitsev, Elkins Park, PA (US); Bi-Sen Ding, New York, NY (US); Douglas B. Cines, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 100 days.

(21) Appl. No.: 12/811,443

(22) PCT Filed: Dec. 31, 2008

(86) PCT No.: PCT/US2008/088632
§ 371 (c)(1),
(2), (4) Date: Jul. 1, 2010

(87) PCT Pub. No.: WO2009/086552
PCT Pub. Date: Jul. 9, 2009

(65) Prior Publication Data
US 2010/0285015 A1    Nov. 11, 2010

Related U.S. Application Data

(60) Provisional application No. 61/018,636, filed on Jan. 2, 2008.

(51) Int. Cl.
*A61K 39/00* (2006.01)
(52) U.S. Cl. ............... 424/185.1; 424/134.1; 424/135.1; 424/145.1; 514/13.5; 514/14.9
(58) Field of Classification Search .................. None
See application file for complete search history.

(56) References Cited

U.S. PATENT DOCUMENTS

| | | | |
|---|---|---|---|
| 4,916,071 A | 4/1990 | Hung et al. | |
| 5,229,367 A | 7/1993 | Perretti et al. | |
| 5,480,869 A | 1/1996 | Wei et al. | |
| 5,653,979 A | 8/1997 | Muzykantov et al. | |
| 6,488,927 B2 | 12/2002 | Muzykantov | |
| 7,041,287 B2 | 5/2006 | Muzykantov | |
| 7,157,087 B2 | 1/2007 | Muzykantov et al. | |
| 7,172,760 B2 | 2/2007 | Muzykantov | |
| 7,250,168 B2 * | 7/2007 | Light et al. | 424/192.1 |
| 7,674,466 B2 | 3/2010 | Muzykantov | |
| 7,816,449 B2 | 10/2010 | Menovcik et al. | |
| 8,088,372 B2 * | 1/2012 | Hosokawa et al. | 424/94.64 |
| 2003/0152563 A1 * | 8/2003 | Muzykantov et al. | 424/93.73 |
| 2006/0140917 A1 | 6/2006 | Muzykantov et al. | |
| 2009/0110741 A1 | 4/2009 | Simone et al. | |
| 2009/0130104 A1 | 5/2009 | Muzykantov et al. | |
| 2009/0258078 A1 | 10/2009 | Muzykantov et al. | |

OTHER PUBLICATIONS

Spitzer et al., Molecular Immunology, 2003, 40:911-919.*
Janeway et al., Immunobiology, 3rd edition, 1997, Garland Publishing, pp. 8:32-8:50.*
Dubel, Isolation of IgG antibody Fv-DNA from various mouse and rat hybridoma cell lines using the polymerase chain reaction with a simple set of primers, Journal of Immunological Methods, May 1994, pp. 89-95, vol. 175, Elsevier Science B.V.
Zaitsev, Sustained thromboprophylaxis mediated by an RBC-targeted pro-urokinase zymogen activated at the site of clot formation, Blood, Apr. 21, 2010, pp. 5241-5248, vol. 115, No. 25, American Society of Hematology.
Zaitsev, et al., Targeting of a Mutant Plasminogen Activator to Circulating Red Blood Cells for Prophylactic Fibrinolysis, JPET, Epub Dec. 1, 2009, vol. 332, No. 3, pp. 1022-1031.
Zaitsev, et al., Targeting recombinant thrombomodulin fusion protein to red blood cells provides multifaceted thromboprophylaxis, Blood, Epub Apr. 4, 2012, vol. 119, pp. 4779-4785.
Abeyama, et al., The N-terminal domain of thrombomodulin sequesters high-mobility group-B1 protein, a novel antiinflammatory mechanism, The Journal of Clinical Investigation, May 2005, pp. 1267-1275, vol. 115.
Auffray, et al., Glycophorin A dimerization and band 3 interaction during erythroid membrane biogenesis: in vivo studies in human glycophorin A transgenic mice, Blood, May 1, 2001, pp. 2872-8, vol. 97(9).
Ding, et al., Advanced Drug Delivery Systems That Target the Vascular Endothelium, Molecular Interventions, Apr. 2006, pp. 98-112, vol. 6, issue 2.
Ganguly, et al., Blood clearance and activity of erythrocyte-coupled fibrinolytics, The Journal of Pharmacology and Experimental Therapeutics, Mar. 2005, pp. 1106-13, vol. 312(3).
Ganguly, et al., Fibrin affinity of erythrocyte-coupled tissue-type plasminogen activators endures hemodynamic forces and enhances fibrinolysis in vivo, The Journal of Pharmacology and Experimental Therapeutics, Mar. 2006, pp. 1130-1136, vol. 316(3).
Ganguly, et al., The glycocalyx protects erythrocyte-bound tissue-type plasminogen activator from enzymatic inhibition, The Journal of Pharmacology and Experimental Therapeutics, Apr. 2007, pp. 158-164, vol. 321(1).
Jenny, et al., A critical review of the methods for cleavage of fusion proteins with thrombin and factor Xa, Protein Expression and Purification, 2003, pp. 1-11, vol. 31.
Mqadmi, et al., Reduced red blood cell destruction by antibody fragments, Immunohematology, 2006, pp. 11-14, vol. 22(1).
Murciano, et al., Prophylactic fibrinolysis through selective dissolution of nascent clots by tPA-carrying erythrocytes, Nature Biotechnology, Epub Jul. 6, 2003, pp: 891-896, vol. 21(8).
Spitzer, et al., ScFv-mediated in vivo targeting of DAF to erythrocytes inhibits lysis by compement, Molecular Immunology, 2003, pp. 911-919, vol. 40.

(Continued)

Primary Examiner — Michael Szperka
(74) Attorney, Agent, or Firm — Howson & Howson LLP

(57) ABSTRACT

Fusion proteins comprising a single chain antigen-binding domain (scFv) of a monoclonal antibody, linked to an anti-thrombotic agent, anti-inflammatory agent, or a pro-drug thereof are provided, where the polypeptide binds to a binding site (antigen) expressed on the surface of a red blood cell at a density greater than 5,000 copies per red blood cell. Pharmaceutical compositions comprising these fusion proteins, and methods of delivering an anti-thrombotic agent to the surface of a red blood cell via delivery of these fusion proteins, and methods of treating or preventing thrombosis, tissue ischemia, acute myocardial infarction (AMI), ischemic stroke, cerebrovascular disease, pulmonary embolism, or ischemic peripheral vascular disease via administration of the fusion proteins or compositions comprising same are also provided.

6 Claims, 24 Drawing Sheets

OTHER PUBLICATIONS

Spitzer, et al., In Vivo Correction of Complement Regulatory Protein Deficiency with an Inhibitor Targeting the Red Blood Cell Membrane, The Journal of Immunology, 2005, pp. 7763-7770, vol. 175.

Spitzer, et al., Properdin can initiate complement activation by binding specific target surfaces and providing a platform for de novo convertase assembly, The Journal of Immunology, Aug. 2007, pp. 179(4):2600-2608.

Zaitsev, et al., Human complement receptor type 1—directed loadingof tissue plasminogen activator on circulating erythrocytes for prophylactic fibrinolysis, Blood, prepublished online May 30, 2006, pp. 1895-1902, vol. 108, No. 6.

International Search Report and Written Opinion from parent International Patent Application No. PCT/US08/88632, mailed Mar. 2, 2009.

* cited by examiner

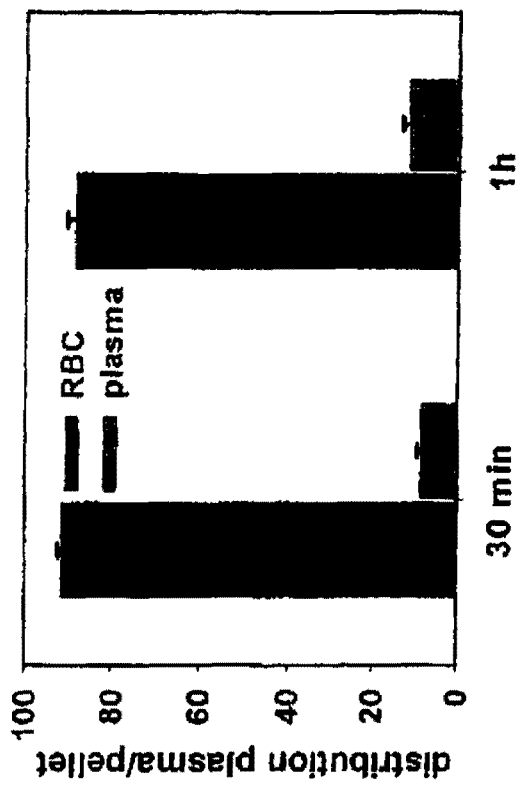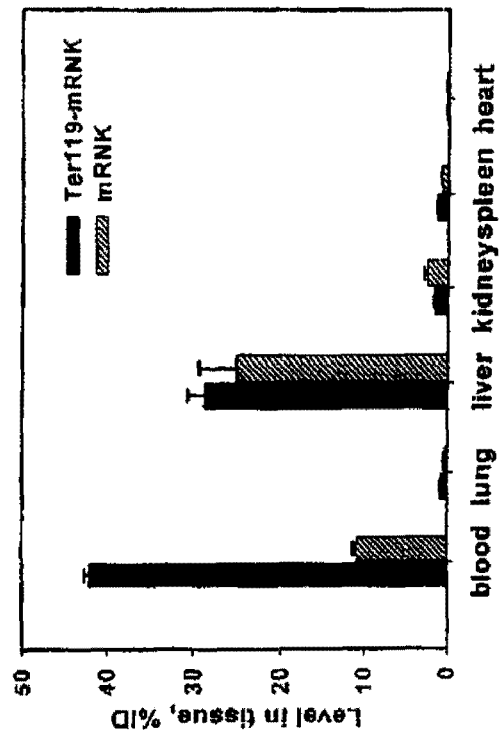
Fig. 5

SEQUENCE LISTING

```
<160> NUMBER OF SEQ ID NOS: 10

<210> SEQ ID NO 1
<211> LENGTH: 13
<212> TYPE: PRT
<213> ORGANISM: Artificial Sequence
<220> FEATURE:
<223> OTHER INFORMATION: synthetic peptide

<400> SEQUENCE: 1

Ser Ser Ser Ser Gly Ser Ser Ser Ser Gly Ala Ala Ala
1               5                   10

<210> SEQ ID NO 2
<211> LENGTH: 15
<212> TYPE: PRT
<213> ORGANISM: Artificial Sequence
<220> FEATURE:
<223> OTHER INFORMATION: synthetic peptide

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: synthetic peptide

<400> SEQUENCE: 3

Met Tyr Pro Arg Gly Asn
1               5

<210> SEQ ID NO 4
<211> LENGTH: 253
<212> TYPE: PRT
<213> ORGANISM: Mus musculus

<400> SEQUENCE: 4

Arg Ser Pro Trp Pro Gly Val Pro Thr Ser Gln Val Lys Leu Gln Glu
1               5                   10                  15

Ser Gly Gly Gly Leu Val Gln Pro Gly Gly Ser Leu Lys Leu Ser Cys
            20                  25                  30

Val Ala Ser Gly Phe Thr Phe Arg Asp His Trp Met Asn Trp Val Arg
        35                  40                  45

Gln Ala Pro Gly Lys Thr Met Glu Trp Ile Gly Asp Ile Arg Pro Asp
    50                  55                  60
```

```
Gly Ser Asp Thr Asn Tyr Ala Pro Ser Val Arg Asn Arg Phe Thr Ile
65                  70                  75                  80

Ser Arg Asp Asn Ala Arg Ser Ile Leu Tyr Leu Gln Met Ser Asn Met
                85                  90                  95

Arg Ser Asp Tyr Thr Ala Thr Tyr Tyr Cys Val Arg Asp Ser Pro Thr
            100                 105                 110

Arg Ala Gly Leu Met Asp Ala Trp Gly Gln Gly Ala Ser Val Thr Val
        115                 120                 125

Leu Thr Gly Gly Gly Gly Ser Gly Gly Gly Gly Ser Gly Gly Gly Gly
    130                 135                 140

Ser Asp Ile Gln Met Ile Gln Ser Pro Ser Val Leu Ser Ala Ser Val
145                 150                 155                 160

Gly Asp Arg Val Thr Leu Asn Cys Lys Ala Ser Gln Asn Ile Asn Lys
                165                 170                 175

Tyr Leu Asn Trp Tyr Gln Gln Lys Leu Gly Glu Ala Pro Lys Val Leu
            180                 185                 190

Ile Tyr Asn Thr Asn Asn Leu Gln Thr Gly Ile Pro Ser Arg Phe Ser
        195                 200                 205

Gly Ser Gly Ser Gly Thr Asp Phe Thr Leu Thr Ile Ser Ser Leu Gln
    210                 215                 220

Pro Glu Asp Phe Ala Thr Tyr Phe Cys Phe Gln His Tyr Thr Trp Pro
225                 230                 235                 240

Thr Phe Gly Gly Gly Thr Lys Leu Glu Leu Lys Arg Ala
                245                 250

<210> SEQ ID NO 5
<211> LENGTH: 266
<212> TYPE: PRT
<213> ORGANISM: Mus musculus

<400> SEQUENCE: 5

Leu Lys Phe Gln Cys Gly Gln Lys Thr Leu Arg Pro Arg Ile Ile Gly
1               5                   10                  15

Gly Glu Phe Thr Thr Ile Glu Asn Gln Pro Trp Phe Ala Ala Ile Tyr
                20                  25                  30

Arg Arg His Arg Gly Gly Ser Val Thr Tyr Val Cys Gly Gly Ser Leu
            35                  40                  45

Ile Ser Pro Cys Trp Val Ile Ser Ala Thr His Cys Phe Ile Asp Tyr
        50                  55                  60

Pro Lys Lys Glu Asp Tyr Ile Val Tyr Leu Gly Arg Ser Arg Leu Asn
65                  70                  75                  80

Ser Asn Thr Gln Gly Glu Met Lys Phe Glu Val Glu Asn Leu Ile Leu
                85                  90                  95

His Lys Asp Tyr Ser Ala Asp Thr Leu Ala His His Asn Asp Ile Ala
            100                 105                 110

Leu Leu Lys Ile Arg Ser Lys Glu Gly Arg Cys Ala Gln Pro Ser Arg
        115                 120                 125

Thr Ile Gln Thr Ile Cys Leu Pro Ser Met Tyr Asn Asp Pro Gln Phe
    130                 135                 140

Gly Thr Ser Cys Glu Ile Thr Gly Phe Gly Lys Glu Asn Ser Thr Asp
145                 150                 155                 160

Tyr Leu Tyr Pro Glu Gln Leu Lys Met Thr Val Val Lys Leu Ile Ser
                165                 170                 175

His Arg Glu Cys Gln Gln Pro His Tyr Tyr Gly Ser Glu Val Thr Thr
            180                 185                 190
```

```
Lys Met Leu Cys Ala Ala Asp Pro Gln Trp Lys Thr Asp Ser Cys Gln
            195                 200                 205

Gly Asp Ser Gly Gly Pro Leu Val Cys Ser Leu Gln Gly Arg Met Thr
        210                 215                 220

Leu Thr Gly Ile Val Ser Trp Gly Arg Gly Cys Ala Leu Lys Asp Lys
225                 230                 235                 240

Pro Gly Val Tyr Thr Arg Val Ser His Phe Leu Pro Trp Ile Arg Ser
                245                 250                 255

His Thr Lys Glu Glu Asn Gly Leu Ala Leu
            260                 265

<210> SEQ ID NO 6
<211> LENGTH: 554
<212> TYPE: PRT
<213> ORGANISM: Mus musculus

<400> SEQUENCE: 6

Arg Arg Pro Trp Pro Gly Val Pro Thr Ser Gln Val Lys Leu Gln Glu
1               5                   10                  15

Ser Gly Gly Gly Leu Val Gln Pro Gly Gly Ser Leu Lys Leu Ser Cys
            20                  25                  30

Val Ala Ser Gly Phe Thr Phe Arg Asp His Trp Met Asn Trp Val Arg
        35                  40                  45

Gln Ala Pro Gly Lys Thr Met Glu Trp Ile Gly Asp Ile Arg Pro Asp
    50                  55                  60

Gly Ser Asp Thr Asn Tyr Ala Pro Ser Val Arg Asn Arg Phe Thr Ile
65                  70                  75                  80

Ser Arg Asp Asn Ala Arg Ser Ile Leu Tyr Leu Gln Met Ser Asn Met
                85                  90                  95

Arg Ser Asp Tyr Thr Ala Thr Tyr Tyr Cys Val Arg Asp Ser Pro Thr
            100                 105                 110

Arg Ala Gly Leu Met Asp Ala Trp Gly Gln Gly Ala Ser Val Thr Val
        115                 120                 125

Leu Thr Gly Gly Gly Gly Ser Gly Gly Gly Ser Gly Gly Gly Gly
    130                 135                 140

Ser Asp Ile Gln Met Ile Gln Ser Pro Ser Val Leu Ser Ala Ser Val
145                 150                 155                 160

Gly Asp Arg Val Thr Leu Asn Cys Lys Ala Ser Gln Asn Ile Asn Lys
                165                 170                 175

Tyr Leu Asn Trp Tyr Gln Gln Lys Leu Gly Glu Ala Pro Lys Val Leu
            180                 185                 190

Ile Tyr Asn Thr Asn Asn Leu Gln Thr Gly Ile Pro Ser Arg Phe Ser
        195                 200                 205

Gly Ser Gly Ser Gly Thr Asp Phe Thr Leu Thr Ile Ser Ser Leu Gln
    210                 215                 220

Pro Glu Asp Phe Ala Thr Tyr Phe Cys Phe Gln His Tyr Thr Trp Pro
225                 230                 235                 240

Thr Phe Gly Gly Gly Thr Lys Leu Glu Leu Lys Arg Ala Ser Ser Ser
                245                 250                 255

Ser Gly Ser Ser Ser Ser Gly Ala Ala Ala Leu Lys Phe Gln Cys Gly
            260                 265                 270

Gln Lys Thr Leu Arg Pro Arg Ile Ile Gly Gly Glu Phe Thr Thr Ile
        275                 280                 285

Glu Asn Gln Pro Trp Phe Ala Ala Ile Tyr Arg Arg His Arg Gly Gly
    290                 295                 300
```

```
Ser Val Thr Tyr Val Cys Gly Gly Ser Leu Ile Ser Pro Cys Trp Val
305                 310                 315                 320

Ile Ser Ala Thr His Cys Phe Ile Asp Tyr Pro Lys Lys Glu Asp Tyr
                325                 330                 335

Ile Val Tyr Leu Gly Arg Ser Arg Leu Asn Ser Asn Thr Gln Gly Glu
            340                 345                 350

Met Lys Phe Glu Val Glu Asn Leu Ile Leu His Lys Asp Tyr Ser Ala
        355                 360                 365

Asp Thr Leu Ala His His Asn Asp Ile Ala Leu Leu Lys Ile Arg Ser
    370                 375                 380

Lys Glu Gly Arg Cys Ala Gln Pro Ser Arg Thr Ile Gln Thr Ile Cys
385                 390                 395                 400

Leu Pro Ser Met Tyr Asn Asp Pro Gln Phe Gly Thr Ser Cys Glu Ile
                405                 410                 415

Thr Gly Phe Gly Lys Glu Asn Ser Thr Asp Tyr Leu Tyr Pro Glu Gln
            420                 425                 430

Leu Lys Met Thr Val Val Lys Leu Ile Ser His Arg Glu Cys Gln Gln
        435                 440                 445

Pro His Tyr Tyr Gly Ser Glu Val Thr Thr Lys Met Leu Cys Ala Ala
    450                 455                 460

Asp Pro Gln Trp Lys Thr Asp Ser Cys Gln Gly Asp Ser Gly Gly Pro
465                 470                 475                 480

Leu Val Cys Ser Leu Gln Gly Arg Met Thr Leu Thr Gly Ile Val Ser
                485                 490                 495

Trp Gly Arg Gly Cys Ala Leu Lys Asp Lys Pro Gly Val Tyr Thr Arg
            500                 505                 510

Val Ser His Phe Leu Pro Trp Ile Arg Ser His Thr Lys Glu Glu Asn
        515                 520                 525

Gly Leu Ala Leu Asp Tyr Lys Asp His Asp Gly Asp Tyr Lys Asp His
    530                 535                 540

Asp Ile Asp Tyr Lys Asp Asp Asp Lys
545                 550

<210> SEQ ID NO 7
<211> LENGTH: 356
<212> TYPE: PRT
<213> ORGANISM: Mus musculus

<400> SEQUENCE: 7

Arg Ser Pro Lys Gly Lys Ser Glu Asp Cys Tyr Val Gly Lys Gly Val
1               5                   10                  15

Thr Tyr Arg Gly Thr His Ser Leu Thr Thr Ser Gln Ala Ser Cys Leu
            20                  25                  30

Pro Trp Asn Ser Ile Val Leu Met Gly Lys Ser Tyr Thr Ala Trp Arg
        35                  40                  45

Thr Asn Ser Gln Ala Leu Gly Leu Gly Arg His Asn Tyr Cys Arg Asn
    50                  55                  60

Pro Asp Gly Asp Ala Arg Pro Trp Cys His Val Met Lys Asp Arg Lys
65                  70                  75                  80

Leu Thr Trp Glu Tyr Cys Asp Met Ser Pro Cys Ser Thr Cys Gly Leu
                85                  90                  95

Arg Gln Tyr Lys Arg Pro Gln Phe Arg Ile Lys Gly Gly Leu Tyr Thr
            100                 105                 110

Asp Ile Thr Ser His Pro Trp Gln Ala Pro Ile Phe Val Ala Ala Ala
        115                 120                 125
```

Ala Ser Pro Gly Glu Arg Phe Leu Cys Gly Gly Val Leu Ile Ser Ser
        130                 135                 140

Cys Trp Val Leu Ser Ala Ala His Cys Phe Leu Glu Arg Phe Pro Pro
145                 150                 155                 160

Asn His Leu Lys Val Val Leu Gly Arg Thr Tyr Arg Val Val Pro Gly
                165                 170                 175

Glu Glu Glu Gln Thr Phe Glu Ile Glu Lys Tyr Ile Val His Glu Glu
            180                 185                 190

Phe Asp Asp Asp Thr Tyr Asp Asn Asp Ile Ala Leu Leu Gln Leu Arg
            195                 200                 205

Ser Gln Ser Lys Gln Cys Ala Gln Glu Ser Ser Val Gly Thr Ala
        210                 215                 220

Cys Leu Pro Asp Pro Asn Leu Gln Leu Pro Asp Trp Thr Glu Cys Glu
225                 230                 235                 240

Leu Ser Gly Tyr Gly Lys His Glu Ala Ser Pro Phe Phe Ser Asp
                245                 250                 255

Arg Leu Lys Glu Ala His Val Arg Leu Tyr Pro Ser Ser Arg Cys Thr
            260                 265                 270

Ser Gln His Leu Phe Asn Lys Thr Val Thr Asn Asn Met Leu Cys Ala
        275                 280                 285

Gly Asp Thr Arg Ser Gly Gly Asn Gln Asp Leu His Asp Ala Cys Gln
290                 295                 300

Gly Asp Ser Gly Gly Pro Leu Val Cys Met Ile Asn Lys Gln Met Thr
305                 310                 315                 320

Leu Thr Gly Ile Ile Ser Trp Gly Leu Gly Cys Gly Gln Lys Asp Val
                325                 330                 335

Pro Gly Val Tyr Thr Lys Val Thr Asn Tyr Leu Asp Trp Ile His Asp
            340                 345                 350

Asn Met Lys Gln
        355

<210> SEQ ID NO 8
<211> LENGTH: 620
<212> TYPE: PRT
<213> ORGANISM: Mus musculus

<400> SEQUENCE: 8

Arg Ser Pro Trp Pro Gly Val Pro Thr Ser Gln Val Lys Leu Gln Glu
1               5                   10                  15

Ser Gly Gly Gly Leu Val Gln Pro Gly Gly Ser Leu Lys Leu Ser Cys
            20                  25                  30

Val Ala Ser Gly Phe Thr Phe Arg Asp His Trp Met Asn Trp Val Arg
        35                  40                  45

Gln Ala Pro Gly Lys Thr Met Glu Trp Ile Gly Asp Ile Arg Pro Asp
    50                  55                  60

Gly Ser Asp Thr Asn Tyr Ala Pro Ser Val Arg Asn Arg Phe Thr Ile
65                  70                  75                  80

Ser Arg Asp Asn Ala Arg Ser Ile Leu Tyr Leu Gln Met Ser Asn Met
                85                  90                  95

Arg Ser Asp Tyr Thr Ala Thr Tyr Tyr Cys Val Arg Asp Ser Pro Thr
            100                 105                 110

Arg Ala Gly Leu Met Asp Ala Trp Gly Gln Gly Ala Ser Val Thr Val
        115                 120                 125

Leu Thr Gly Gly Gly Gly Ser Gly Gly Gly Gly Ser Gly Gly Gly Gly
    130                 135                 140

```
Ser Asp Ile Gln Met Ile Gln Ser Pro Ser Val Leu Ala Ser Val
145                 150                 155                 160

Gly Asp Arg Val Thr Leu Asn Cys Lys Ala Ser Gln Asn Ile Asn Lys
            165                 170                 175

Tyr Leu Asn Trp Tyr Gln Gln Lys Leu Gly Glu Ala Pro Lys Val Leu
            180                 185                 190

Ile Tyr Asn Thr Asn Asn Leu Gln Thr Gly Ile Pro Ser Arg Phe Ser
            195                 200                 205

Gly Ser Gly Ser Gly Thr Asp Phe Thr Leu Thr Ile Ser Ser Leu Gln
        210                 215                 220

Pro Glu Asp Phe Ala Thr Tyr Phe Cys Phe Gln His Tyr Thr Trp Pro
225                 230                 235                 240

Thr Phe Gly Gly Gly Thr Lys Leu Glu Leu Lys Arg Ala Ser Ser Ser
                245                 250                 255

Ser Gly Ser Ser Ser Ser Gly Ala Ala Ala Pro Lys Gly Lys Ser Glu
            260                 265                 270

Asp Cys Tyr Val Gly Lys Gly Val Thr Tyr Arg Gly Thr His Ser Leu
            275                 280                 285

Thr Thr Ser Gln Ala Ser Cys Leu Pro Trp Asn Ser Ile Val Leu Met
    290                 295                 300

Gly Lys Ser Tyr Thr Ala Trp Arg Thr Asn Ser Gln Ala Leu Gly Leu
305                 310                 315                 320

Gly Arg His Asn Tyr Cys Arg Asn Pro Asp Gly Asp Ala Arg Pro Trp
                325                 330                 335

Cys His Val Met Lys Asp Arg Lys Leu Thr Trp Glu Tyr Cys Asp Met
            340                 345                 350

Ser Pro Cys Ser Thr Cys Gly Leu Arg Gln Tyr Lys Arg Pro Gln Phe
        355                 360                 365

Arg Ile Lys Gly Gly Leu Tyr Thr Asp Ile Thr Ser His Pro Trp Gln
370                 375                 380

Ala Pro Ile Phe Val Ala Ala Ala Ser Pro Gly Glu Arg Phe Leu
385                 390                 395                 400

Cys Gly Gly Val Leu Ile Ser Ser Cys Trp Val Leu Ser Ala Ala His
                405                 410                 415

Cys Phe Leu Glu Arg Phe Pro Pro Asn His Leu Lys Val Val Leu Gly
            420                 425                 430

Arg Thr Tyr Arg Val Val Pro Gly Glu Glu Glu Gln Thr Phe Glu Ile
        435                 440                 445

Glu Lys Tyr Ile Val His Glu Glu Phe Asp Asp Thr Tyr Asp Asn
450                 455                 460

Asp Ile Ala Leu Leu Gln Leu Arg Ser Gln Ser Lys Gln Cys Ala Gln
465                 470                 475                 480

Glu Ser Ser Ser Val Gly Thr Ala Cys Leu Pro Asp Pro Asn Leu Gln
                485                 490                 495

Leu Pro Asp Trp Thr Glu Cys Glu Leu Ser Gly Tyr Gly Lys His Glu
            500                 505                 510

Ala Ser Ser Pro Phe Phe Ser Asp Arg Leu Lys Glu Ala His Val Arg
        515                 520                 525

Leu Tyr Pro Ser Ser Arg Cys Thr Ser Gln His Leu Phe Asn Lys Thr
    530                 535                 540

Val Thr Asn Asn Met Leu Cys Ala Gly Asp Thr Arg Ser Gly Gly Asn
545                 550                 555                 560

Gln Asp Leu His Asp Ala Cys Gln Gly Asp Ser Gly Gly Pro Leu Val
```

-continued

```
                    565                 570                 575
Cys Met Ile Asn Lys Gln Met Thr Leu Thr Gly Ile Ile Ser Trp Gly
            580                 585                 590
Leu Gly Cys Gly Gln Lys Asp Val Pro Gly Val Tyr Thr Lys Val Thr
                595                 600                 605
Asn Tyr Leu Asp Trp Ile His Asp Asn Met Lys Gln
            610                 615                 620

<210> SEQ ID NO 9
<211> LENGTH: 501
<212> TYPE: PRT
<213> ORGANISM: Mus musculus

<400> SEQUENCE: 9

Leu Ser Ala Leu Ala Lys Leu Gln Pro Thr Gly Ser Gln Cys Val Glu
1               5                   10                  15
His Glu Cys Phe Ala Leu Phe Gln Gly Pro Ala Thr Phe Leu Asp Ala
            20                  25                  30
Ser Gln Ala Cys Gln Arg Leu Gln Gly His Leu Met Thr Val Arg Ser
        35                  40                  45
Ser Val Ala Ala Asp Val Ile Ser Leu Leu Leu Ser Gln Ser Ser Met
    50                  55                  60
Asp Leu Gly Pro Trp Ile Gly Leu Gln Leu Pro Gln Gly Cys Asp Asp
65                  70                  75                  80
Pro Val His Leu Gly Pro Leu Arg Gly Phe Gln Trp Val Thr Gly Asp
                85                  90                  95
Asn His Thr Ser Tyr Ser Arg Trp Ala Arg Pro Asn Asp Gln Thr Ala
            100                 105                 110
Pro Leu Cys Gly Pro Leu Cys Val Thr Val Ser Thr Ala Thr Glu Ala
        115                 120                 125
Ala Pro Gly Glu Pro Ala Trp Glu Glu Lys Pro Cys Glu Thr Glu Thr
    130                 135                 140
Gln Gly Phe Leu Cys Glu Phe Tyr Phe Thr Ala Ser Cys Arg Pro Leu
145                 150                 155                 160
Thr Val Asn Thr Arg Asp Pro Glu Ala Ala His Ile Ser Ser Thr Tyr
                165                 170                 175
Asn Thr Pro Phe Gly Val Ser Gly Ala Asp Phe Gln Thr Leu Pro Val
            180                 185                 190
Gly Ser Ser Ala Ala Val Glu Pro Leu Gly Leu Glu Leu Val Cys Arg
        195                 200                 205
Ala Pro Pro Gly Thr Ser Glu Gly His Trp Ala Trp Glu Ala Thr Gly
    210                 215                 220
Ala Trp Asn Cys Ser Val Glu Asn Gly Cys Glu Tyr Leu Cys Asn
225                 230                 235                 240
Arg Ser Thr Asn Glu Pro Arg Cys Leu Cys Pro Arg Asp Met Asp Leu
                245                 250                 255
Gln Ala Asp Gly Arg Ser Cys Ala Arg Pro Val Val Gln Ser Cys Asn
            260                 265                 270
Glu Leu Cys Glu His Phe Cys Val Ser Asn Ala Glu Val Pro Gly Ser
        275                 280                 285
Tyr Ser Cys Met Cys Glu Thr Gly Tyr Gln Leu Ala Ala Asp Gly His
    290                 295                 300
Arg Cys Glu Asp Val Asp Asp Cys Lys Gln Gly Pro Asn Pro Cys Pro
305                 310                 315                 320
Gln Leu Cys Val Asn Thr Lys Gly Gly Phe Glu Cys Phe Cys Tyr Asp
```

```
                    325                 330                 335
Gly Tyr Glu Leu Val Asp Gly Glu Cys Val Glu Leu Leu Asp Pro Cys
            340                 345                 350

Phe Gly Ser Asn Cys Glu Phe Gln Cys Gln Pro Val Ser Pro Thr Asp
        355                 360                 365

Tyr Arg Cys Ile Cys Ala Pro Gly Phe Ala Pro Lys Pro Asp Glu Pro
    370                 375                 380

His Lys Cys Glu Met Phe Cys Asn Glu Thr Ser Cys Pro Ala Asp Cys
385                 390                 395                 400

Asp Pro Asn Ser Pro Thr Val Cys Glu Cys Pro Glu Gly Phe Ile Leu
            405                 410                 415

Asp Glu Gly Ser Val Cys Thr Asp Ile Asp Glu Cys Ser Gln Gly Glu
        420                 425                 430

Cys Phe Thr Ser Glu Cys Arg Asn Phe Pro Gly Ser Tyr Glu Cys Ile
    435                 440                 445

Cys Gly Pro Asp Thr Ala Leu Ala Gly Gln Ile Ser Lys Asp Cys Asp
    450                 455                 460

Pro Ile Pro Val Arg Glu Asp Thr Lys Glu Glu Gly Ser Gly Glu
465                 470                 475                 480

Pro Pro Val Ser Pro Thr Pro Gly Ser Pro Thr Gly Pro Pro Ser Ala
            485                 490                 495

Arg Pro Val His Ser
            500

<210> SEQ ID NO 10
<211> LENGTH: 789
<212> TYPE: PRT
<213> ORGANISM: Mus musculus

<400> SEQUENCE: 10

Arg Ser Pro Trp Pro Gly Val Pro Thr Ser Gln Val Lys Leu Gln Glu
1               5                   10                  15

Ser Gly Gly Gly Leu Val Gln Pro Gly Gly Ser Leu Lys Leu Ser Cys
            20                  25                  30

Val Ala Ser Gly Phe Thr Phe Arg Asp His Trp Met Asn Trp Val Arg
        35                  40                  45

Gln Ala Pro Gly Lys Thr Met Glu Trp Ile Gly Asp Ile Arg Pro Asp
    50                  55                  60

Gly Ser Asp Thr Asn Tyr Ala Pro Ser Val Arg Asn Arg Phe Thr Ile
65                  70                  75                  80

Ser Arg Asp Asn Ala Arg Ser Ile Leu Tyr Leu Gln Met Ser Asn Met
            85                  90                  95

Arg Ser Asp Tyr Thr Ala Thr Tyr Tyr Cys Val Arg Asp Ser Pro Thr
        100                 105                 110

Arg Ala Gly Leu Met Asp Ala Trp Gly Gln Gly Ala Ser Val Thr Val
    115                 120                 125

Leu Thr Gly Gly Gly Gly Ser Gly Gly Gly Ser Gly Gly Gly Gly
130                 135                 140

Ser Asp Ile Gln Met Ile Gln Ser Pro Ser Val Leu Ser Ala Ser Val
145                 150                 155                 160

Gly Asp Arg Val Thr Leu Asn Cys Lys Ala Ser Gln Asn Ile Asn Lys
            165                 170                 175

Tyr Leu Asn Trp Tyr Gln Gln Lys Leu Gly Glu Ala Pro Lys Val Leu
        180                 185                 190

Ile Tyr Asn Thr Asn Asn Leu Gln Thr Gly Ile Pro Ser Arg Phe Ser
```

```
                195                 200                 205
Gly Ser Gly Ser Gly Thr Asp Phe Thr Leu Thr Ile Ser Ser Leu Gln
    210                 215                 220

Pro Glu Asp Phe Ala Thr Tyr Phe Cys Phe Gln His Tyr Thr Trp Pro
225                 230                 235                 240

Thr Phe Gly Gly Gly Thr Lys Leu Glu Leu Lys Arg Ala Ser Ser Ser
                245                 250                 255

Ser Gly Ser Ser Ser Ser Gly Ala Ala Ala Leu Ser Ala Leu Ala Lys
            260                 265                 270

Leu Gln Pro Thr Gly Ser Gln Cys Val Glu His Glu Cys Phe Ala Leu
        275                 280                 285

Phe Gln Gly Pro Ala Thr Phe Leu Asp Ala Ser Gln Ala Cys Gln Arg
    290                 295                 300

Leu Gln Gly His Leu Met Thr Val Arg Ser Ser Val Ala Ala Asp Val
305                 310                 315                 320

Ile Ser Leu Leu Leu Ser Gln Ser Ser Met Asp Leu Gly Pro Trp Ile
                325                 330                 335

Gly Leu Gln Leu Pro Gln Gly Cys Asp Asp Pro Val His Leu Gly Pro
            340                 345                 350

Leu Arg Gly Phe Gln Trp Val Thr Gly Asp Asn His Thr Ser Tyr Ser
        355                 360                 365

Arg Trp Ala Arg Pro Asn Asp Gln Thr Ala Pro Leu Cys Gly Pro Leu
    370                 375                 380

Cys Val Thr Val Ser Thr Ala Thr Glu Ala Ala Pro Gly Glu Pro Ala
385                 390                 395                 400

Trp Glu Glu Lys Pro Cys Glu Thr Glu Thr Gln Gly Phe Leu Cys Glu
                405                 410                 415

Phe Tyr Phe Thr Ala Ser Cys Arg Pro Leu Thr Val Asn Thr Arg Asp
            420                 425                 430

Pro Glu Ala Ala His Ile Ser Ser Thr Tyr Asn Thr Pro Phe Gly Val
        435                 440                 445

Ser Gly Ala Asp Phe Gln Thr Leu Pro Val Gly Ser Ser Ala Ala Val
    450                 455                 460

Glu Pro Leu Gly Leu Glu Leu Val Cys Arg Ala Pro Pro Gly Thr Ser
465                 470                 475                 480

Glu Gly His Trp Ala Trp Glu Ala Thr Gly Ala Trp Asn Cys Ser Val
                485                 490                 495

Glu Asn Gly Gly Cys Glu Tyr Leu Cys Asn Arg Ser Thr Asn Glu Pro
            500                 505                 510

Arg Cys Leu Cys Pro Arg Asp Met Asp Leu Gln Ala Asp Gly Arg Ser
        515                 520                 525

Cys Ala Arg Pro Val Val Gln Ser Cys Asn Glu Leu Cys Glu His Phe
    530                 535                 540

Cys Val Ser Asn Ala Glu Val Pro Gly Ser Tyr Ser Cys Met Cys Glu
545                 550                 555                 560

Thr Gly Tyr Gln Leu Ala Ala Asp Gly His Arg Cys Glu Asp Val Asp
                565                 570                 575

Asp Cys Lys Gln Gly Pro Asn Pro Cys Pro Gln Leu Cys Val Asn Thr
            580                 585                 590

Lys Gly Gly Phe Glu Cys Phe Cys Tyr Asp Gly Tyr Glu Leu Val Asp
        595                 600                 605

Gly Glu Cys Val Glu Leu Leu Asp Pro Cys Phe Gly Ser Asn Cys Glu
    610                 615                 620
```

```
Phe Gln Cys Gln Pro Val Ser Pro Thr Asp Tyr Arg Cys Ile Cys Ala
625                 630                 635                 640

Pro Gly Phe Ala Pro Lys Pro Asp Glu Pro His Lys Cys Glu Met Phe
            645                 650                 655

Cys Asn Glu Thr Ser Cys Pro Ala Asp Cys Asp Pro Asn Ser Pro Thr
            660                 665                 670

Val Cys Glu Cys Pro Glu Gly Phe Ile Leu Asp Glu Gly Ser Val Cys
        675                 680                 685

Thr Asp Ile Asp Glu Cys Ser Gln Gly Glu Cys Phe Thr Ser Glu Cys
    690                 695                 700

Arg Asn Phe Pro Gly Ser Tyr Glu Cys Ile Cys Gly Pro Asp Thr Ala
705                 710                 715                 720

Leu Ala Gly Gln Ile Ser Lys Asp Cys Asp Pro Ile Pro Val Arg Glu
            725                 730                 735

Asp Thr Lys Glu Glu Glu Gly Ser Gly Glu Pro Pro Val Ser Pro Thr
            740                 745                 750

Pro Gly Ser Pro Thr Gly Pro Pro Ser Ala Arg Pro Val His Ser Asp
        755                 760                 765

Tyr Lys Asp His Asp Gly Asp Tyr Lys Asp His Asp Ile Asp Tyr Lys
    770                 775                 780

Asp Asp Asp Asp Lys
785
```

TARGETING RECOMBINANT THERAPEUTICS TO CIRCULATING RED BLOOD CELLS

BACKGROUND OF THE INVENTION

Many pathological processes such as thrombosis and hemorrhages, systemic inflammation and cytokine shock, pathologies of transport of lipids and other biological compounds, are initiated or/and develop in the blood. Accordingly, activity of therapeutic agents for optimal interventions in these processes must be localized in this compartment. However, most drugs do not circulate for a sufficient time in the bloodstream because of their uptake by liver, renal filtration and diffusion into the tissues via a vascular wall that is permeable for many therapeutic agents via active and passive transport across endothelium and peri-cellular permeability of endothelial monolayer. Current means for retention of drugs in the bloodstream, such as PEG-ylation or encapsulation into PEG-ylated drug carriers (e.g., liposomes) improve their blood solubility and inhibit recognition by the immune system, thus prolonging their longevity in circulation. However, all previous means for drug retention in bloodstream, including PEG-technology, employed relatively small compounds and carriers (e.g., liposomes of ~100 nm diameter) that can diffuse in tissues (leading to side effects and drug elimination) and uptake by clearing organs (liver and kidney). Therefore, despite relatively easy access to many pathological targets in blood, repeated administrations of high doses of a drug are needed to compensate for clearance. This complicates therapies and leads to adverse effects. The general problem of inadequate therapeutic interventions in the pathological processes in blood has not been resolved.

For example, hemostasis, the sealing of damaged blood vessels by mural clots, prevents bleeding. Thrombosis, pathological intravascular occlusion by clots, can cause tissue ischemia and damage leading to acute myocardial infarction (AMI), ischemic stroke, pulmonary embolism and ischemic peripheral vascular disease, among other conditions. Thrombosis is the leading cause of mortality and disability in the United States. Thrombi are prone to recur within hours to days after an AMI or stroke and the risk is great after transient ischemic attack or pulmonary embolism and in immobilized patients. Thrombosis is also a common and dangerous complication of surgery that is especially difficult to manage due to the risk of acute bleeding at the operative site. Invasive interventions (e.g., angioplasty and carotid endarterectomy) may be complicated by formation of small clots that embolize to the brain and cause neurological dysfunction.

Therefore, situations in which patients are at highest risk for occurrence or recurrence of thrombosis, and means to identify such high-risk patients are known. Nevertheless, safety and efficacy of current prevention and management of thrombosis attained with current anti-thrombotic agents (ATAs) and means for their delivery remain inadequate. Anti-platelet and anticoagulant agents provide only limited prophylaxis and pose considerable risk of bleeding. Emergency therapy of thrombosis employs vascular injection of plasminogen activators (PAs), proteases (MW 30-60 kD) that generate plasmin, which cleaves fibrin clots and thus restores perfusion. However, inadequate circulation time (blood clearance within <15 min), inactivation by plasma inhibitors such as PAI-1 and impermeability of occlusive clots restrict the effectiveness of therapeutic fibrinolysis by PAs. Significant pharmacological doses of a PA (e.g., ~100 mg of tissue type plasminogen activator, tPA) are needed to overcome its inefficiency and achieve fibrinolysis locally. As a result, excess drug diffuses into hemostatic mural clots within minutes after infusion, causing bleeding into tissues. Bleeding into the CNS may cause cerebral hemorrhage. In addition, tPA diffusing into the CNS causes neuronal toxicity and inflammation in the brain. Due to the risk of bleeding and collateral CNS damage, fibrinolytics and anti-coagulants are not used in the post-operative period and in over 95% of stroke patients.

In addition, the only currently employed use of PA, i.e., post-thrombosis, is marred by inevitable delays (time needed for diagnosis, transportation, injection and clot dissolution, slowed by clot impermeability). This delay increases the risk of ischemia-reperfusion (I/R) injury that worsens outcome. Unfortunately, available prophylactic drugs (e.g., anticoagulants and thrombin inhibitors) do not provide adequate protection against thrombosis. First, they are not completely effective due to redundancy of thrombotic mechanisms (e.g., anticoagulants do not prevent platelet activation and anti-platelet agents do not inhibit coagulation). Second, many prophylactic agents altering metabolism of pro-coagulant factors (e.g., inhibitors of the synthesis of vitamin-K dependent coagulation factors, warfarin) require a substantial time to develop an effect (e.g., approximately 36 hours after warfarin administration). Such time frames are not suitable for thromboprophylaxis in acute settings. Third, all of these drugs predispose to bleeding (in addition to other side effects), resulting in a high danger of bleeding, which limits drug utility and dosing especially in the acute settings.

PAs currently in use cannot be used for prophylaxis because of their unfavorable pharmacokinetics and therefore the need to administer potentially dangerous doses of drug for a prolonged period of time. At clinically relevant doses, these PAs cleave fibrin in both hemostatic as well as newly formed clots, which predisposes to bleeding, whereas their penetration into the surrounding tissues causes toxic effects including collateral damage in the central nervous system (CNS).

Targeting of ATAs to clot components (e.g., by chemical conjugation or recombinant fusion with antibodies or antibody fragments that bind to fibrin or activated platelets) does not obviate the failure of ATAs to distinguish between hemostatic and pathological thrombi. In addition, these ATAs with high affinity to clots less effectively permeate into the clots due to enhanced retention on the clot surface, which impedes thrombolysis.

Other research has involved the targeting of plasminogen activators to the vascular lumen (endothelial targeting) using a PECAM-1 single-chain scFv (Ding, et al., Blood 2005, 106(13):4191-4198. See also Ding, et al., Molecular Interventions April 2006, 6(2): 98-112). Targeting of ATAs, such as PAs, to the surface of endothelium by means of fusion proteins consisting of anti-cell adhesion molecule (anti-CAM) scFvs and ATAs may be employed for a prophylactic administration of PAs, which would preferentially dissolve newly formed pathological clots in the vascular area of interest, hence reduce danger of hemorrhage caused by dissolution of existing hemostatic clots. This approach seems ideal for prophylaxis of local thromboses after ischemia or reperfusion, such as in organ transplantation. Nevertheless, this approach is also not ideal for thromboprophylaxis of many other pro-thrombotic states (AMI, TIA, PE). Targeting of CAMs on endothelium is relevant only to highly vascularized organs such as lungs. Also, targeting to CAMs cannot fully prevent endocytosis or transcytosis of ATA from luminal to adventitial side of the vessels which will decrease the duration of the prophylactic effect of the drug.

By targeting ATAs, such as PAs, to red blood cells (RBCs), which can be attained by chemical conjugation of ATAs with antibodies that bind to RBCs, the half-life of the drug in circulation can be prolonged from minutes to days. ATA/RBC complexes selectively lyse newly formed clots because they are incorporated during clot development, and their size prevents penetration of pre-existing clots. This drastically diminishes the risk of bleeding. In addition, coupling to a RBC prevents drug permeation into tissues including the CNS.

However, this approach for selective lysis of newly formed clots has several disadvantages for clinical application. For example, current anti-CR1 conjugates (e.g., anti-CR1/tPA, targeted to a specific RBC determinant, CR-1), such as those described in Zaitsev, et al. (Blood, 108(6):1895-1902 (May 30, 2006)) are not preferred therapeutically for a number a reasons, in addition to those described in the preceding paragraph. Furthermore, the CR1 expression level in humans varies from 300 to 1,500 copies per RBC and ~15% of humans are CR1 negative. Therefore, targeting CR1 may provide insufficient dosing in some cases and will not be useful in CR1-negative patients. Targeting of a highly expressed determinant on RBC with bivalent antibodies can cause RBC aggregation. Therefore, this approach maybe useful only for targeting ATAs to low-abundance RBC determinants, which limits dosing that may be insufficient in the cases of excessive thromboses. Also, Fc fragment of antibodies can activate complement, promote clearance or signal through Fc receptors or induce an immune response in the host. The synthetic chemistry limits yield and homogeneity of the ATA/antibody conjugates, thereby restricting their clinical utility.

In addition, thrombosis is closely intertwined with vascular inflammation. In many cases one of these conditions leads to another and both mutually propagate each other, further aggravating the outcome.

There exists a need for safe and clinically applicable compositions for effective treatment of thrombosis and associated pathological conditions including vascular inflammation.

SUMMARY OF THE INVENTION

The compositions and methods described herein provide a solution to the acute unmet medical need for design of new drug delivery systems aimed at safer and more effective management of thrombosis. These compositions and methods provide clear advantages over existing compositions and methods for treatment with anti-thrombotic agents (ATAs). These compositions and methods also provide clear advantages over existing compositions and methods for treatment with anti-inflammatory drugs or agents. Further, these compositions and methods provide a novel delivery system for the administration of pro-drugs useful in treating thrombosis and other medical conditions.

In one aspect, a fusion protein is provided that comprises a single chain antigen-binding domain (scFv) of a monoclonal antibody linked to an anti-thrombotic agent (ATA), anti-inflammatory agent, or a pro-drug thereof, where the scFv binds to a determinant (e.g., binding site, antigen) expressed on the surface of a red blood cell at a density greater than 5,000 copies per red blood cell. In certain embodiments these fusion proteins also contain a cleavage site.

In another aspect, a fusion protein is provided that comprises a single chain antigen-binding domain (scFv) linked to an anti-thrombotic agent, anti-inflammatory agent, or a pro-drug thereof, wherein the scFv binds a determinant expressed on the surface of a red blood cell, and the determinant is not a specific site for recognition by host defense cells that clear microscopic objects from surface of circulating RBC without damage to the RBC.

In a further aspect, a fusion protein is provided which comprises a single chain antigen-binding domain (scFv) linked to an anti-thrombotic agent, anti-inflammatory agent, or a pro-drug thereof, wherein at least 10% of the fusion protein injected into the bloodstream is maintained on the surface of a red blood cell in vivo for at least 48 hours.

In another aspect, a fusion protein is provided which binds a pro-inflammatory mediator, e.g., HMGB1.

In yet another aspect, pharmaceutical compositions are provided that comprise one or more of these above-described fusion proteins.

In yet a further aspect, methods of delivering an anti-thrombotic agent or anti-inflammatory agent to the surface of a red blood cell via delivery of a fusion protein, as described above, are also provided. Methods of treating or preventing thrombosis, tissue ischemia, acute myocardial infarction (AMI), ischemic stroke, cerebrovascular disease, pulmonary embolism, sepsis, acute lung injury (ALI) or other forms of vascular inflammation, or ischemic peripheral vascular disease via administration of the fusion proteins or compositions comprising same, are similarly provided.

In another aspect, methods of delivering an anti-inflammatory agent to the surface of a red blood cell via delivery of a fusion protein, as described above, are also provided.

In still another aspect, methods of delivering a pro-drug to the surface of a red blood cell via delivery of a fusion protein, as described above, are also provided.

Also provided is the use of any of these fusion proteins or compositions comprising same as a medicament.

BRIEF DESCRIPTION OF THE DRAWINGS

FIGS. 4A and 4B represent binding at 10% hematocrit, while FIGS. 4C and 4D represent binding at 1% hemotocrit. Binding procedure was performed with $^{125}$I labeled fusion proteins.

FIGS. 5A and 5B are bar graphs showing the biodistribution of Ter119-mRNK in vivo. For these experiments, 2-5 µg of $^{125}$I radiolabeled fusion protein or control non-targeted mRNK were injected intravenously to wild type (WT) mice. One hour later, tissue uptake was determined. FIG. 5A is a bar graph showing the percentage of injected dose per tissue (% ID). Ter119-mRNK showed a greatly higher level in blood than mRNK, due to binding to RBC. The latter statement is validated by FIG. 5B, a bar graph showing the distribution of Ter119-mRNK in blood (RBC vs plasma) at different time points. More than 90% of Ter119-mRNK are associated with RBC at 30 min and 60 min of circulation.

DETAILED DESCRIPTION OF THE INVENTION

The compositions and methods described herein meet the needs in the art.

I. The Fusion Protein

Fusion proteins are provided which comprise a single chain antigen-binding domain (scFv) linked to an anti-thrombotic agent, anti-inflammatory agent, or a pro-drug, wherein said scFv binds to a determinant (e.g., binding site, antigen) expressed on the surface of a red blood cell at a density greater than 5,000 copies per red blood cell. The scFv is linked to a native or genetically or otherwise modified polypeptide chain of an anti-thrombotic agent (ATA), anti-inflammatory agent, or pro-drug thereof. For example, the recombinant fusion proteins as described herein are useful particularly for thromboprophylaxis in patients at risk of thrombus formation.

In one embodiment, the fusion protein optionally contains a cleavage site interposed between the scFv and the anti-thrombotic agent/anti-inflammatory agent to permit release of the therapeutic molecule at the site of a pathological condition (pro-drug construct). In this embodiment, the cleavage site is introduced for the purpose of releasing the anti-thrombotic/anti-inflammatory agent from the RBC at a desired site. Using this modular recombinant format, one of skill in the art can design and synthesize a series of monovalent, Fc-fragment free, and homologous proteins carrying diverse anti-thrombotic/anti-inflammatory drugs directed to diverse RBC determinants, which are easy to produce, maintain quality control, store and administer, as described in detail below.

A. The scFv of the Fusion Protein

The fusion proteins contain a targeting single chain antigen-binding domain (scFv) that binds to a determinant expressed on the surface of a red blood cell at a density greater than 5,000 copies per red blood cell. Use of an scFv (monovalent) avoids cross-linking of binding sites or determinants, thereby avoiding potentially harmful cell membrane modification and cell aggregation.

Figure 1:
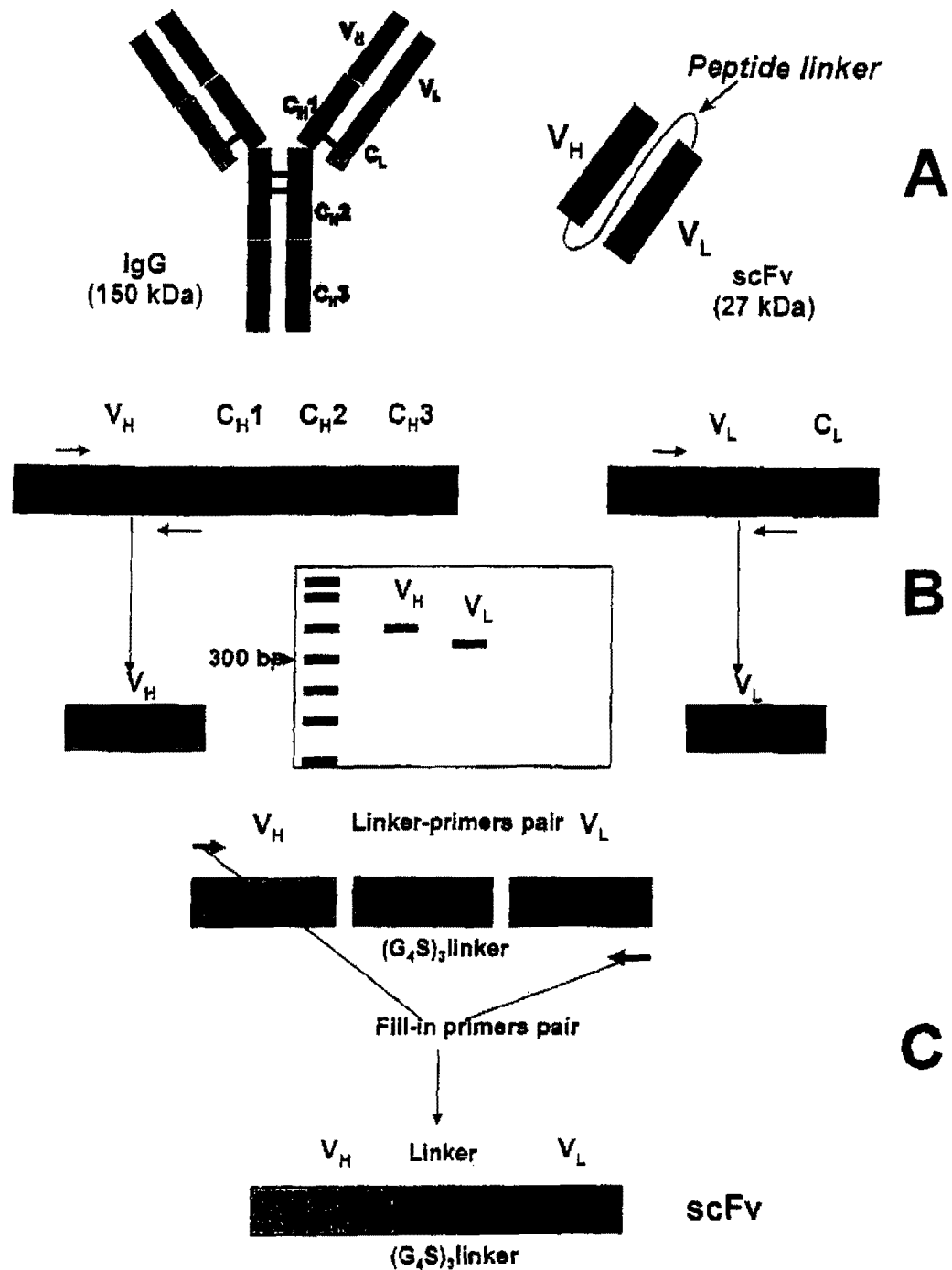
FIG. 1A provides a general description of an antibody structure (having variable heavy and light chains, e.g., $V_H$ and $V_L$, and constant heavy and light chains, e.g., $C_H$ and $C_L$), and derived scFv molecular structure with a peptide linker between the $V_H$ and $V_L$.
FIG. 1B reflects RT PCR (reverse transcription polymerase chain reaction) amplification of $V_H$ and $V_L$ chains of the antibody from total RNA of a corresponding hybridoma cell line. The $V_H$, $V_L$, and linker fragments are then fused by PCR to form the resulting scFv (FIG. 1C).
Figure 2:
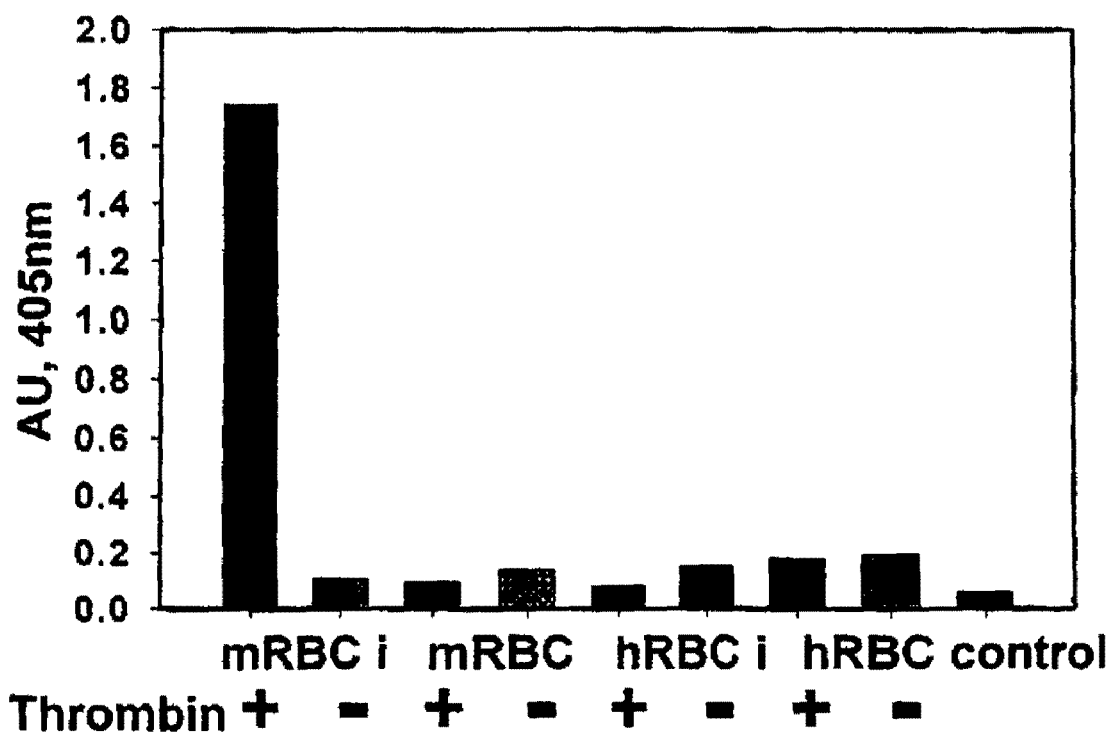
FIG. 2 is a bar graph showing the functional activity of a fusion protein comprising an anti-glycophorin A associated protein (expressed on mouse RBC) scFv derived from parental rat MAb Ter119 as described in FIG. 1, and an extracellular domain of mouse thrombomodulin (Ter119-TM). Mouse and human RBCs were incubated in serum free medium from induced and non-induced S2 cells transfected with a plasmid encoding Ter119-TM. RBC were washed and incubated with protein C in the presence or absence of thrombin. The experiment demonstrated that only mRBC loaded with Ter119-TM in the presence of thrombin cause protein C activation thus confirming both determinant binding and functional activity of Ter119-TM. The columns are marked as induced murine RBC (mRBC i) with (+) or without (−) thrombin; non-induced murine RBC (mRBC) with (+) or without (−) thrombin; induced human RBC (hRBC i) with (+) or without (−) thrombin; non-induced human RBC (hRBC) with (+) or without (−) thrombin; and control.

Use of recombinant proteins, which are synthesized as an scFv, has an advantage over chemical conjugation with respect to each of the above-noted problems in the art. For example, recent research has included the use of scFv-mediated targeting of human complement regulatory protein (CRP) decay-accelerating factor (DAF) to a red blood cell restricted surface antigen of the mouse (Spitzer, et al., Mol. Immunol. 2003, 40:911-919).

scFvs may be generated conventionally, e.g., by the method of Spitzer, et al. (Mol. Immunol. 2003, 40:911-919). Total RNA of a hybridoma cell line is isolated (e.g., by RNeasy, Qiagen, Velencia, Calif.), followed by reverse transcription, e.g., using the SMART™ technology (Clontech, Palo Alto, Calif.) employing known primers (e.g., those of Dübel, et al. (J. Immunol. Methods 1994, 175:89-95)). The resulting heavy ($V_H$) and light ($V_L$) chain variable cDNA fragments are then subcloned into a suitable plasmid, e.g., pCR®2.1-TOPO® (Invitrogen, Carlsbad, Calif.). The materials utilized are not a limitation of these embodiments. The $V_H$ and $V_L$ chains generated are combined with a suitable linker, resulting in the desired scFv (see, e.g., Example 1). In one embodiment, an scFv is prepared as illustrated in FIG. 1. Since scFv fusion proteins are monovalent, they are not anticipated to cross-link RBC determinants, which is the main safety concern for using most monoclonal antibodies. Lack of Fc-fragment and deletion of unnecessary domains in the protein drug entity enhances specificity and safety of interventions.

The determinant to which the single chain antigen-binding domain (scFv) of the fusion protein binds is any determinant expressed on the surface of a red blood cell, preferably a human RBC, in a sufficient density. In one embodiment, the cell surface determinant is expressed across the human population at a density greater than 5,000 molecules per red blood cell. In another embodiment, the cell surface determinant is expressed across the human population at a density greater than 10,000 molecules per red blood cell. In another embodiment, the cell surface determinant is expressed across the human population at a density greater than 20,000 molecules per red blood cell. In still another embodiment, the cell surface determinant is expressed across the human population at a density greater than 50,000 molecules per red blood cell. In another embodiment, the cell surface determinant is expressed on the red blood cell at greater than 100,000 molecules per red blood cell. In another embodiment, the cell surface determinant is expressed on the red blood cell at greater than 500,000 molecules per red blood cell. In still further embodiments, the determinant is expressed on the surface of a red blood cell at a density greater than 1,000,000 molecules per red blood cell. In still further embodiments, the determinant is expressed on the surface of a red blood cell at a density greater than 2,000,000 molecules per red blood cell.

In a specific embodiment, the determinant is glycophorin A associated protein (GPA). This is the mouse-specific analog of human glycophorin A, recognized by a rat monoclonal antibody Ter119, and is thus the GPA used in the mouse models provided within the Examples, infra. One of skill in the art will recognize that 'GPA' is often used in the literature to specifically refer to the glycophorin A antigen. Accordingly, for clarity, the specific antigen human glycophorin A is designated hGPA herein.

Preferably the anti-GPA antibody from which the scFv is obtained is an anti-human GPA antibody. The level of GPA expression in humans is ~$10^6$ copies per RBC across the population. Thus, the use of anti-GPA scFv in the fusion proteins described herein provides a viable therapeutic composition due to its wider range of RBC loading. This enables strict dosage control of the anti-thrombotic agent, which is not available for constructs for which determinant density is lower. The anti-thrombotic and anti-inflammatory protein thrombomodulin is also demonstrated in such fusion proteins.

In another embodiment, the determinant is an ABO blood group antigen. Thus, suitable seFvs for use in the fusion proteins described herein include scFv to GPA or ABO blood group antigens. In another embodiment, the scFv is to RBC band 3 antigen. Still other appropriate determinants meeting the above density requirements may be selected by one of ordinary skill in the art.

In another embodiment, the binding site or cell surface determinant is not a specific site for recognition by host defense cells that clear microscopic objects from the surface of a red blood cell without damage to the red blood cell. Both the GPA and ABO blood group antigens meet this requirement. In contrast, CR1 antigen does not meet this requirement.

However, while scFvs to the determinants GPA or ABO blood group antigens are one example of scFvs useful in the fusion proteins, other scFvs capable of binding to the designed determinant on a RBC may be used in place thereof. One of skill in the art provided with the teachings of this specification and publically available information can readily design an svFv useful in the fusion proteins described herein.

B. The Anti-Thrombotic Agent, Anti-Inflammatory Agent, or Pro-Drug Thereof of the Fusion Protein Fusion proteins described herein may contain any anti-thrombotic agent (molecule), anti-inflammatory agent, or pro-drug thereof for which targeting to a red blood cell is desired for purposes of systemic delivery, or alternatively, for delivery to the site of a pathological condition including conditions characterized by the production or presence of an enzyme that can cleave the anti-thrombotic agent, anti-inflammatory agent, or the pro-drug, from the fusion protein.

As used herein, the term "pro-drug" or "prodrug" encompasses any polypeptide encoding an anti-thrombotic or anti-inflammatory agent and a cleavage site for activation of the agent. The pro-drug is inactive (or significantly less active) upon administration, and is metabolized in vivo into an active form. In further embodiments, the pro-drug is a pro-drug of an anti-thrombotic or anti-inflammatory agent.

In one embodiment, the anti-thrombotic agent is one that is capable of producing its therapeutic effect when attached to the RBC, i.e., an active anti-thrombotic agent. In another embodiment, the anti-thrombotic agent is a pro-drug which contains a native or synthetic cleavage site and which produces an active anti-thrombotic effect only upon cleavage from its pro-drug state.

Among such anti-thrombotic agents include without limitation, plasminogen activators. In still a further embodiment, the plasminogen activator is tPA, urokinase, tenectase, retavase, streptokinase, staphylokinase, or a plasminogen activator from venoms and saliva of bats, insects, and other animals. In another embodiment, the plasminogen activator is anistreplase, pro-urokinase (pUK), or a hybrid plasminogen activator (e.g., as described in U.S. Pat. No. 4,916,071).

In a further embodiment the anti-thrombotic agent is the low molecular weight single chain urokinase-like plasminogen activator described in the examples below (also termed uPA (as the exemplary plasminogen activator), lUK, lmwUK, and lmw scuPA within the examples). Also included are mutants or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule. In a further embodiment, the anti-thrombotic agent contains a moiety presented by a protease domain of a plasminogen activator. Naturally-occurring pro-drugs of these agents may be employed. Synthetically designed prodrugs based on these agents may also be employed in the fusion proteins. Prodrugs containing modified cleavage sites may also be employed as part of the fusion protein.

In one embodiment, the therapeutic molecule or pro-drug is a therapeutic protein or pro-drug of an anti-inflammatory agent. In one embodiment, the anti-inflammatory agent is an antibody against a cytokine or other pro-inflammatory mediator. In a further embodiment, the anti-inflammatory agent may comprise a moiety presented by thrombomodulin or a domain thereof. Among other anti-inflammatory agents for use in the fusion proteins described herein are, without limitation, somatostatin, adiponectin, cortistatin, corticotrophin releasing factor, sauvagine, nocifensins, as well as the anti-inflammatory cytokines, IL-1 receptor antagonist (IL-1ra), IL-4, IL-6, IL-10, and IL-13 and the soluble receptors sTNFRI, sTNFRp55, sTNFRII, sTNFRp75, sIL-1RII, mIL-1RII, and IL-18BP, among others. Anti-inflammatory proteins may be native or mutated proteins. Similarly, native, mutated or synthetic anti-inflammatory peptides, including without limitation, peptides described in U.S. Pat. Nos. 5,480,869; 7,816, 449 and 5,229,367, among other known peptides may also form part of the fusion proteins described herein. One of skill in the art may select or design an appropriate anti-inflammatory agent or prodrug depending on the pathological condition being treated.

In still another embodiment, the therapeutic molecule is molecule which binds a pro-inflammatory mediator. In one embodiment, the pro-inflammatory mediator is the HMGB1 cytokine. In this embodiment, signaling by HMGB1 is disrupted by binding of the lectin-like domain of thrombomodulin (abbreviated herewith as TM). In other embodiments, the pro-inflammatory cytokine is IL-1-α, IL-1-β, IL-6, TNF-α, TGF-β, LIF, IFN-γ, OSM, CNTF, GM-CSF, IL-8, IL-11, IL-12, IL-17, and IL-18.

In one embodiment, a fusion protein may contain a therapeutically-active site, domain or moiety of any of the anti-thrombotic agents, anti-inflammatory agents, or pro-drugs listed herein or known to the art to be suitable for direct targeted administration to the site of a thrombus. Other useful pro-drugs known to one of skill in the art may be used herein.

In still other embodiments, mutations in protein sequence of the anti-thrombotic agent or anti-inflammatory agent, therapeutically-active site, domain, or moiety thereof allows its conversion into a pro-drug activated and/or released locally at a desired pathological sites (e.g., pathological nascent intravascular thrombi) using specific activity of pathological factors that exist only in these pathological sites, such as protease thrombin. Such mutations in the amino acid sequences or nucleotide sequences encoding the therapeutic protein can be employed to insert a desired cleavage, enzymatic or activation site into the therapeutic molecule, or into or adjacent the linker between the scFv and the therapeutic molecule in the fusion protein. Alternatively, such mutations can change a native cleavage site to another desired cleavage site, or to insert a cleavage site where none naturally existed into or adjacent to a therapeutic molecule.

In one embodiment, the therapeutic pro-drug molecule is activated or the mature drug molecule released from the fusion protein by an enzyme, which level is locally elevated under pathological conditions. In a further embodiment, the enzyme is a protease. In still further embodiments, the protease is a leukocyte protease (e.g., cathepsin), an activated protease in the coagulation cascade (e.g., activated Factor Xa), or an activated protease in the complement cascade. In other embodiments, the protease's activity is elevated locally in tissue. In still other embodiments, the protease is a metalloproteinase, elastase, or collagenase.

In still other embodiments of fusion proteins containing therapeutic pro-drug molecules, the enzyme is a pathological mediator. In further embodiments, the pathological mediator is involved in coagulation or fibrinolysis. In another embodiment, the pathological mediator is thrombin or plasmin. In a further embodiment, the pathological mediator is thrombin. Thus, for example, in one embodiment, the therapeutic pro-drug molecule is the thrombin activatable low molecular weight single chain urokinase-like plasmin activator, described in the examples below. In another embodiment, the therapeutic pro-drug molecule is thrombin-activatable thrombomodulin, or thrombin-activatable tPA (or its mouse analog, mRNK-T).

In other embodiments, the pathological mediator is a pro-inflammatory mediator, such as a pro-inflammatory cytokine (IL-1-α, IL-1-β, IL-6, TNF-α, TGF-β, LIF, IFN-γ, OSM, CNTF, GM-CSF, IL-11, IL-12, IL-17, or IL-18). In other embodiments, the pro-inflammatory mediator is a complement protein or prostaglandin. Still other pro-inflammatory mediators are known in the art and may be used.

C. The Linker Between the scFv and Anti-Thrombotic Agent, Anti-Inflammatory Agent, or Pro-Drug Thereof The fusion protein as described herein is prepared by linking (fusing) the above-described scFv capable of binding a determinant expressed on the surface of a red blood cell to the above-described anti-thrombotic agent, anti-inflammatory agent, or pro-drug molecule. Moreover, genetic engineering allows the design and synthesis of targeted pro-drugs which can be cleaved by pathophysiologically relevant enzymes that are generated at the size of disease that cannot be attained using chemical conjugation.

As noted above, linkers may also be utilized to join variable heavy and variable light chain fragments. A linker as used herein refers to a chain of as short as about 1 amino acid to as long as about 100 amino acids, or longer. In a further embodiment, the linker is 3, 4, 5, 6, 7, 8, 9, 10, 11, 12, 13, 14, 15, 16, 17, 18, 19, or 20 amino acids in length. In one embodiment, the linker is 13 amino acids in length.

In one embodiment, the linker is -Ser-Ser-Ser-Ser-Gly-Ser-Ser-Ser-Gly-Ala-Ala-Ala-, i.e., "$(S_4G)_2AAA$" (SEQ ID NO: 1). In another embodiment, the linker is $(G_4S)_3$, i.e., -Gly-Gly-Gly-Gly-S-Gly-Gly-Gly-Gly-S-Gly-Gly-Gly-Gly-S- (SEQ ID NO: 2)(see Böldicke, et al. (Stem Cells 2001, 19:24-36)). However, as will be understood by one of skill in the art, other linkers can be utilized.

Further, a cleavage sequence, such as the thrombin-sensitive cleavage sequence or other enzyme cleavage sequence, can be inserted in the linker to provide for release of the drug when the RBC to which it is targeted encounters the appropriate cleaving enzyme at the site of the pathological condition, e.g., upon active thrombosis. This cleavage sequence may be located within a linker or at a terminus thereof. In one embodiment, a thrombin cleavage site -Met-Tyr-Pro-Arg-Gly-Asn- (SEQ ID NO: 3) may be inserted in, or appended to, the linker between the scFv and the therapeutic molecule or pro-drug. In another embodiment, the thrombin cleavage site is Pro-Arg. In still a further embodiment, lack of the native Phe-Lys plasmin cleavage site prevents single chain (sc) uPA activation (into fully active two-chain plasminogen activator (tcuPA)) via plasmin.

In another embodiment, antibody-derived scFv with a thrombin releasing site can be cloned by an upstream primer, which anneals to the carboxy terminus and introduces the sequence including a short peptide linker with the thrombin cleavage site. In still another embodiment, the cleavage site is internal to the pro-drug itself.

II. Methods of Preparation and Specific Embodiments

The sequences, proteins, and fragments of the fusion proteins described herein may be produced by any suitable means, including recombinant production, chemical synthesis, or other synthetic means. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.*, 85:2149 (1962); Stewart and Young, Solid Phase Peptide Synthesis (Freeman, San Francisco, 1969) pp. 27-62). Polymerase chain reaction (PCR) and related techniques are described in Derbyshire, et al. (Immunochemistry 1: A practical approach. M. Turner, A. Johnston eds., Oxford University Press 1997, e.g., at pp. 239-273). Plasmids useful herein have been described in Derbyshire, et al. (cited above), as well as Gottstein, et al. (Biotechniques 30: 190-200, 2001). Cloning techniques are also described in these and other suitable production methods are within the knowledge of those of skill in the art and are not a limitation of the compositions and methods described herein. Generation of recombinant proteins provides flexibility in design, rapid production, large-scale production and uniform composition.

III. Pharmaceutical Compositions and Methods of Administration

Pharmaceutical compositions containing a fusion protein described herein and a pharmaceutically acceptable carrier or vehicle as described herein are useful for the treatment of a variety of diseases and disorders, depending upon the selection and identity of the anti-thrombosis agent, anti-inflammatory agent, or pro-drug, and the optional enzymatic cleavage site of the fusion protein. In one embodiment, a composition comprises a pharmaceutically acceptable vehicle for intravenous administration. In another embodiment, a composition comprises a pharmaceutically acceptable vehicle for administration via other vascular routes, including but not limited to, intra-arterial and intra-ventricular administration, as well as routes providing slower delivery of drugs to the bloodstream such as intramuscular administration to an animal in need thereof. As used herein, the terms "animal" and "patient" include any mammal. In a further embodiment, the terms "animal" and "patient" refer to a human.

In one embodiment, the fusion proteins described herein may be delivered intraperitoneally. Stable and prolonged loading of fusion protein on red blood cells is demonstrated in Example 14C.

Pharmaceutically acceptable vehicles/carriers include any of those conventionally used in the art, e.g., saline, phosphate buffered saline (PBS), or other liquid sterile vehicles accepted for intravenous injections in clinical practice. Pharmaceutical compositions may also include buffers, pH adjusting agents, and other additives conventionally used in medicine. In one embodiment, compositions described herein are administered systemically as a bolus intravenous injection of a single therapeutic dose of the fusion protein. In a further embodiment, the dose is 0.1-5.0 mg/kg. In another embodiment, the dose is 0.01-0.5 mg/kg.

In other embodiments, methods of delivering an anti-thrombotic agent to the surface of a red blood cell are provided comprising delivering a fusion protein as described herein, or a pharmaceutical composition described herein, to a blood vessel. In one embodiment, fusion proteins are administered via a systemic intravascular route, e.g., a vascular catheter. In some embodiments, rapid targeting of an organ or system may be accomplished by delivery via coronary artery (e.g., for prophylaxis of acute myocardial infarction (AMI)) or the cerebral artery (e.g., for prophylaxis of stroke and other cerebrovascular thrombotic events). Further, the fusion proteins described herein may be administered prophylactically, i.e., in patients predisposed to thrombosis. In a further embodiment, the fusions proteins may be administered to an organ donor, utilized with an isolated organ transplant (e.g., via perfusion), or used with vascular stents.

Intravenous administration of these fusion proteins results in: i) rapid binding of the drug to circulating RBC without altering its biocompatibility; ii) drastically prolonged circulation of the drug as a blood cell-bound complex, iii) limited drug penetration into the blood vessel or surrounding tissues, minimizing attendant side effects and, iv) unique features of local activation in the site of pathology. In one embodiment, at least 10% of a fusion protein described herein is maintained on the surface of a red blood cell in vivo for at least 24 to 48 hours following administration. In another embodiment at least 20% of a fusion protein described herein is maintained on the surface of a red blood cell in vivo for at least 24 to 48 hours following administration. In another embodiment at least 30% of a fusion protein described herein is maintained on the surface of a red blood cell in vivo for at least 24 to 48 hours following administration. In another embodiment at least 40% of a fusion protein described herein is maintained on the surface of a red blood cell in vivo for at least 24 to 48 hours following administration. In another embodiment at least 50% of a fusion protein described herein is maintained on the surface of a red blood cell in vivo for at least 24 to 48 hours following administration. In another embodiment at least 60% of a fusion protein described herein is maintained on the surface of a red blood cell in vivo for at least 24 to 48 hours following administration. In another embodiment at least 70% of a fusion protein described herein is maintained on the surface of a red blood cell in vivo for at least 24 to 48 hours following administration.

Thus, in one embodiment, methods of treating or preventing a cardiovascular disorder, such as thrombosis, tissue ischemia, AMI, ischemic stroke, pulmonary embolism, sepsis, acute lung injury (ALI) or other type of vascular inflammation, or ischemic peripheral vascular disease, involves administering a fusion protein as described herein, or a pharmaceutical composition as described herein, to a blood vessel in a mammal in need thereof. In such disorders, the anti-thrombotic or anti-inflammatory agent and its dosage in delivery (i.e., the amount fused to an individual RBC may be selected and adjusted by an attending physician with regard to the nature of the disorder, the physical condition of the patient, and other such factors). The selection of the cleavage site in the fusion protein may also be selected to match the disorder, e.g., a thrombin cleavage site suitable for most cardiovascular disorders. Loading red blood cells (RBC) in vivo with anti-thrombotic agents (ATAs) constitutes a new approach to thromboprophylaxis that holds promise for improving the management of patients at high risk of thrombosis for a defined period of time in whom anticoagulation poses an unacceptable risk. Delivery of plasminogen activators (PAs) and thrombomodulin (TM) via RBCs markedly prolongs intravascular lifespan and restricts vascular and tissue damage.

In one embodiment, the compositions described herein are effective in the treatment or prevention of cerebrovascular thrombi. In a further embodiment, the compositions described herein are effective in the treatment or prevention of cerebrovascular disease, such as transient ischemic attack and stroke.

Similarly, in another embodiment, methods of treating or preventing disseminated intravascular coagulation (DIC), sepsis, acute lung injury (ALUARDS), aseptic systemic inflammation, and other inflammatory conditions are provided by administering the appropriately designed fusion protein, according to the teachings of this specification.

In the same manner, novel fusion proteins containing a selected pro-drug can be designed according to the teachings herein and employed to treat a variety of disorders in addition to those identified above.

Also provided is the use of a fusion protein or a pharmaceutical composition as described herein as a medicament. The use of a fusion protein or a pharmaceutical composition as described herein to treat any of the above conditions.

IV. EXAMPLES

The examples that follow do not limit the scope of the embodiments described herein. One skilled in the art will appreciate that modifications can be made in the following examples which are intended to be encompassed by the spirit and scope of the invention.

Example 1

Generation of a Single Chain Antigen-Binding Domain (scFv) Molecule

Generation of a single chain antigen-binding domain (scFv) molecule is illustrated in FIG. 1. scFvs are generated in accordance with the teachings herein, as well as those of Spitzer, et al. (Mol. Immunol. 2003, 40:911-919). Total RNA of a hybridoma cell line is isolated (e.g., by RNeasy, Qiagen, Velencia, Calif.). RNA is reverse transcribed, e.g., using the SMART™ technology (Clontech, Palo Alto, Calif.) employing known primers (e.g., those of Dübel, et al. (J. Immunol. Methods 1994, 175:89-95)). The resulting heavy ($V_H$) and light ($V_L$) chain variable cDNA fragments are subcloned into a suitable plasmid, e.g., the pCR®2.1-TOPO® (Invitrogen, Carlsbad, Calif.). Plasmids are then transfected into E. coli. $V_H$ and $V_L$ chains are then isolated by conventional techniques, e.g., agarose gel column or gel electrophoresis.

$V_H$ and $V_L$ chains are combined with a suitable linker, e.g., a $(G_4S)_3$ linker (SEQ ID NO: 2) (Böldicke, et al. (Stem Cells 2001, 19:24-36)) resulting in the desired scFv. PCR-derived sequences are verified by DNA sequencing. The amino acid primary sequence may be analyzed to determine complementarity determining regions (CDRs) by application of the rules described at: Antibody Structure and Sequence Information V2.0 (http://www.rubic.rdg.ac.uk).

Example 2

Generation of a Pro-Drug scFv Fusion Protein

An scFv (RBC epitope binding) is prepared as described in Example 1. A thrombin cleavage site (PR, i.e., Pro-Arg) is cloned into a $(S_4G)_2AAA$ (SEQ ID NO: 1) linker peptide (internally, or at its N- or C-terminus), and the resulting peptide is used to link the $V_L$ domain of the scFv to the low molecular weight single chain urokinase-like plasmin activator. The thrombin cleavage site (PR) cloned in the linker peptide allows the release of single chain urokinase-like plasmin activator from RBC/fusion protein complex during clot formation.

Example 3

Generation of a Non-Releasable scFv-Plasminogen Activator (uPA) Fusion Protein Recombinant anti-Ter119scFv [anti-GPA (glycophorin A associated protein)] was produced as described in Example 1. A plasmid (pcDNA3, (Dr. Atkinson, Washington University, St. Louis) encoding Ter119-scFv (SEQ ID NO: 4) was utilized. Primers were designed via conventional techniques, and two PCR amplifications were performed. The first amplification was of DNA encoding the scFv, adding DNA encoding the $(S_4G)_2AAA$ (SEQ ID NO: 1) linker to its C terminus. The second amplication was of DNA encoding uPA (SEQ ID NO: 5). Both amplified segments were ligated together into the pMT/BipN5HisA plasmid (Invitrogen), with the Ter-119scFv portion N-terminal to the uPA sequence.

Ter119scFv-uPA (SEQ ID NO: 6) was expressed in pMT/BipN5HisA plasmid in Drosophila S2 cells (Drosophila DS2 expression System (Invitrogen)).

Example 4

Mouse Anti-Glycophorin A Associated Protein scFv Thrombin-Releasable Ter119-lmwUK-t (uPA-T)

A fusion protein was prepared according by the method of Examples 2 and 3 comprising an anti-glycophorin A associated protein (mouse RBC) scFv derived from parental rat MAb Ter119 as illustrated in FIG. 1, and thrombin activatable low molecular weight single chain urokinase-like plasmin activator (Ter119-lmwUK-T). Casein zymography indicated that fusion protein by itself had very low plasminogen activation capacity. Thrombin activation lead to a dramatic increase of plasminogen conversion activity. Binding capacity of the fusion protein was confirmed by capture of the fusion protein from the induced S2 cell serum free medium on RBC ghosts from different species. Only mouse RBC ghosts (membranes) were able to pull Ter119-lmwUK-T from the medium (lane 2), which confirmed the specificity of binding.

Example 5

Generation of a Non-Releasable scFv-Plasminogen Activator (mRNK) Fusion Protein A ~70 kDa Ter119scFv/mRNK fusion protein was expressed in Drosophila S2 cells (Drosophila DS2 expression System, (Invitrogen)). Recombinant anti-Ter119scFv [anti- GPA (glycophorin A associated protein)] was produced as described in Example 1. A plasmid (pcDNA3, (Dr. Atkinson, Washington University, St. Louis) encoding Ter119-scFv (SEQ ID NO: 4) was utilized. Primers were designed via conventional techniques, and two PCR amplifications were performed. The first amplification was of DNA encoding the scFv, adding DNA encoding the $(S_4G)_2AAA$ (SEQ ID NO: 1) linker to its C terminus. The second amplication was of DNA encoding mRNK (SEQ ID NO: 7). Both amplified segments were ligated together into the pMT/BipN5HisA plasmid (Invitrogen), with the Ter-119scFv portion N-terminal to the uPA sequence.

Ter119scFv-mRNK (SEQ ID NO: 8) was expressed in pMT/BipN5HisA plasmid in *Drosophila* S2 cells (Drosophila DS2 expression System (Invitrogen)). Expression of the Ter119-mRNK fusion protein was confirmed via Western Blot with anti-mRNK. mRNK control was run against the Ter119-mRNK protein, and predicted ~40 kDa and 70 kDa bands were identified, respectively.

Example 6

Generation of an Expressed Thrombin-Releasable scFv-mRNK Fusion Protein

An scFv-mRNK is prepared as described in Example 5. However, a thrombin cleavage site (PR) is encoded within the $(S_4G)_2AAA$ linker peptide (internally, or at its N- or C-terminus) that links the scFv to mRNK (see Example 2). The thrombin cleavage site cloned in the linker peptide allows the release of mRNK from the RBC/fusion protein complex during clot formation.

Example 7

Generation of an Expressed scFv-TM (Thrombomodulin) Fusion Protein

Recombinant anti-Ter119scFv [anti-GPA (glycophorin A associated protein)] was produced as described in Example 1. A plasmid (pcDNA3 (Dr. Atkinson, Washington University, St. Louis)) encoding Ter119-scFv (SEQ ID NO: 4) was utilized. Primers were designed via conventional techniques, and two PCR amplifications were performed. The first amplification was of DNA encoding the scFv, adding DNA encoding the $(S_4G)_2AAA$ (SEQ ID NO: 1) linker to its C terminus. The second amplication was of DNA encoding TM (thrombomodulin) (SEQ ID NO: 9). Both amplified segments were ligated together into the pMT/BipN5HisA plasmid (Invitrogen), with the Ter-119scFv portion N-terminal to the uPA sequence.

Ter119scFv-TM (SEQ ID NO: 10) was expressed in pMT/BipN5HisA plasmid in *Drosophila* S2 cells (Drosophila DS2 expression System (Invitrogen)).

Example 8

Mouse Anti-Glycophorin A Associated Protein scFv Thrombin-Releasable Ter119-TM An scFv-mRNK is prepared as described in Example 7. However, a thrombin cleavage site (PR) is encoded within the $(S_4G)_2AAA$ linker peptide (internally, or at its N- or C-terminus) that links the scFv to TM (see Example 2). The thrombin cleavage site cloned in the linker peptide allows the release of mRNK from the RBC/fusion protein complex during clot formation.

Mouse and human RBCs were incubated in serum free medium from induced and non-induced S2 cells transfected with a plasmid encoding Ter119-TM. RBC were washed and incubated with protein C in the presence or absence of thrombin. The experiment demonstrated that only mRBC loaded with Ter119-TM in the presence of thrombin cause protein C activation, thus confirming both determinant binding and functional activity of Ter119-TM.

Example 9

Binding of the scFv/Fusion to Ter-119

A. Ter119scFv-mRNK was prepared according to Example 5. mRNK was radiolabeled with $^{125}I$—Na (Perkin Elmer, Wellesley, Mass.) using Iodogen (Pierce, Rockford, Ill.). Mouse and human red blood cells (mRBC and hRBC, suspended to 10% hematocrit) were loaded at the same concentration with Ter119scFv-mRNK by incubation for one hour at 37° C. Unbound ligand was removed via centrifugation with PBS-BSA (phosphate buffered saline-bovine serum albumin) and RBC-bound radioactivity was measured in a γ-counter (Perkin Elmer).

Specific binding to mRBC was revealed (20,000 molecules/mRBC vs. ~120 molecules/hRBC).

B. Ter119scFv-TM fusion protein was prepared according to Example 7.

1. Agglutination (Aggregation) Assay

Mouse and human RBCs were washed in PBS/3% BSA buffer, resuspended in the same buffer to 10% hematocrit and incubated with Ter119-TM (final concentration 40 mg/μl) for 1 h. Binding experiments show that such conditions of incubation provide loading of mRBC with ~20000 molecules of fusion protein/mRBC. Then cells were washed 3 times with PBS/BSA buffer and equimolar amount of mouse HMGB1 (produced in *E. coli* (Sigma)) was added to the assay for 30 min at room temperature. Then RBC were washed with PBS/BSA and brought to the final hematocrit of 1% and the monoclonal Ab to mouse HMGB1 (Sigma, dilution as per manufacturer) was added to the assay placed into a V-shaped plate (total volume−100 μl). After 40 min the V-shaped plate aggregation picture was documented by photography: only mRBC loaded with Ter119-TM and incubated with HMGB1 and appropriate ABs showed the tendency for aggregation thus confirming the late cytokine (HMGB1) scavenging capacity of Ter119-TM fusion protein in RBC-bound state.

Only Ter119scFv-TM loaded RBCs incubated with HMGB1 and then polyclonal anti-HMGB1 antibody aggregated. This result confirms that the thrombomodulin domain of the scFv-TM fusion binds the pro-inflammatory mediator HMGB1.

2. Western Blot confirmed Ter119scFv-TM's binding to HMGB1, as well as Ter119's specificity for mouse red blood cells. Mouse and human RBCs isolated from the fresh heparinated blood were washed with PBS/BSA buffer as described above and brought to the final 10% hematocrit. Both types of cells were incubated in the medium from *Drosophila* S2 cells expressing Ter119-TM for 1 h (the protein production was confirmed by WB (data not shown), then washed 3 times with PBS/BSA and incubated with equimolar concentration of HMGB1 (*E. coli* produced protein, Sigma) for 1 h at room temperature. Then cells were washed 3 times with PBS and lysed in isotonic buffer in order to obtain RBC ghosts. RBC ghosts were washed 3 times by centrifugation in 5 mM phosphate buffer to remove the hemoglobin and finally lysed in a lysis buffer. The lysates from experimental mRBC and hRBC as well as the lysates from intact mRBC and hRBC in equal amount of total loaded protein were run on SDS-PAGE and transferred to Nitrocellulose membrane for WB analyses (The sample of recombinant HMGB1 (Sigma) served as a positive control). The membrane was probed with the monoclonal Abs to HMGB1 followed with the detection with HRP-conjugated anti-mouse-mAbs. The experiment clearly shows that only mRBCs loaded with Ter119-TM were able to pull HMGB1 from the experimental essay.

Example 10

Activity of Expressed scFv-TM (Thrombomodulin) Fusion Protein

A Ter119scFv-TM (SEQ ID NO: 10) was prepared according to Example 7. Mouse and human red blood cells (mRBC and hRBC, suspended to 10% hematocrit) were loaded with Ter119scFv-TM by incubation for one hour at 37° C. Unbound ligand was removed via centrifugation with PBS-BSA (phosphate buffered saline-bovine serum albumin). Loaded and intact (non-loaded) RBC were incubated with thrombin and protein C. Activation of protein C was measured by spectrazyme assay at λ450.

Only mRBC incubated with Ter119-TM caused activation of protein C in the presence of thrombin. This result confirms the binding specificity of Ter119-TM and the functional activity of Ter119-TM when bound to the red blood cell.

Example 11

Effect of Concentration (at Varying Hematocrit Percentages) on scFv Binding

Figure 4:
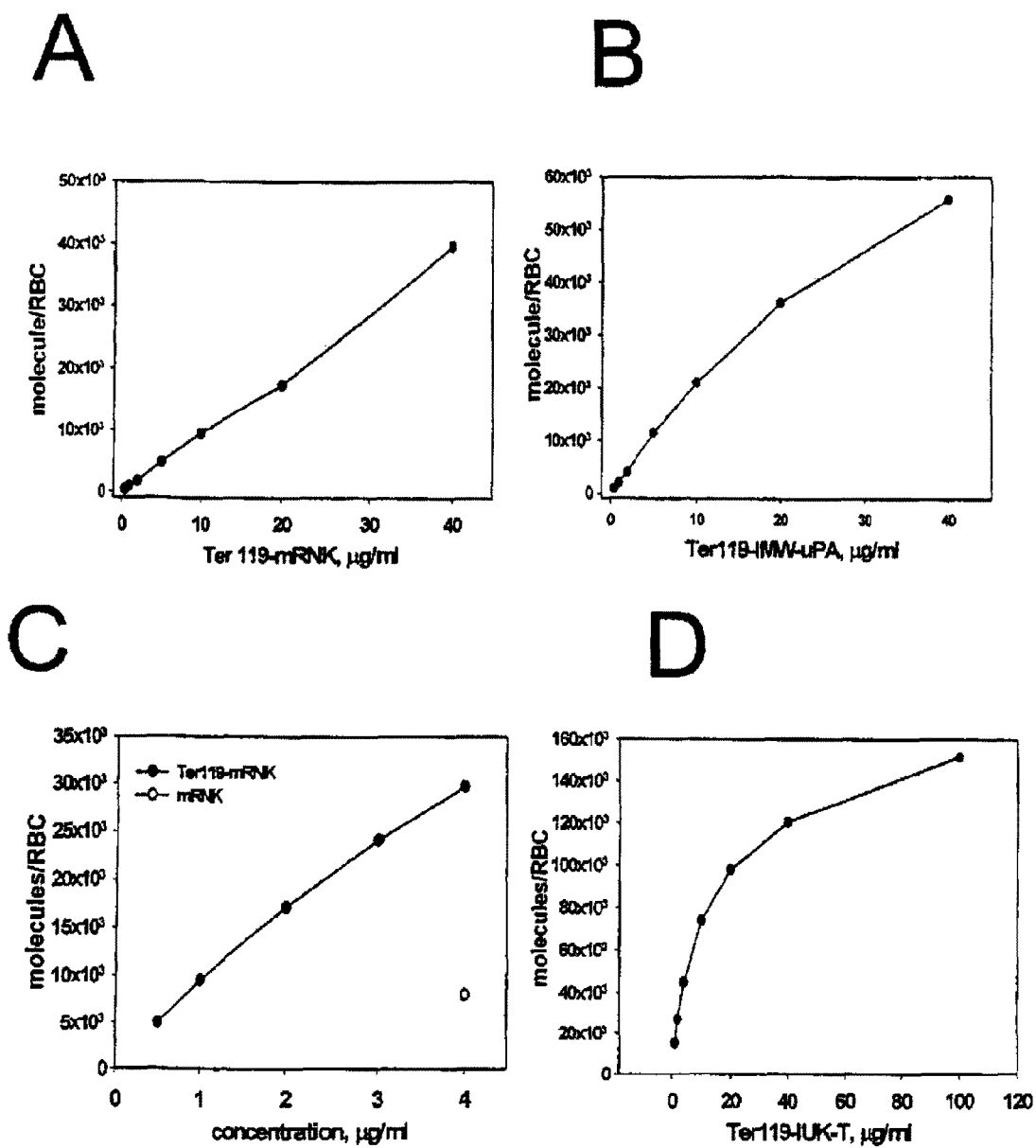
FIGS. 4A through 4D illustrate binding of Ter119-lmvUK-T or Ter119-mRNK to mouse RBC under different percentages of hematocrit.

A. Ter119-mRNK (prepared according to Example 5) or Ter119-lmwUK-T (prepared according to Example 4) $^{125}$I labeled fusion proteins (see Example 9 for labeling method) were bound to mouse red blood cells (mRBCs) at 10% hematocrit [FIGS. 4A (mRNK) and 4B (lmwUK-T)] and 1% hematocrit [FIGS. 4C (mRNK) and 4D (lmwUK-T)]. FIG. 4C reflects the negative control (free mRNK).

Approximate $B_{max}$ (~80,000 molecules/RBC) and $K_d$ (~77.9 nM) was calculated from the data reflected in FIG. 4C (mRNK, 1% hematocrit). This reflects high-affinity, high capacity binding to RBC. More accurate $B_{max}$ and $K_d$ values may be obtained with more diluted suspensions (lower hematocrit), but would be less physiologically relevant, given normal blood hematocrit levels in humans.

B. Using the same protocol as 'A' (above), Ter119scFv-TM (prepared according to Example 7) was tested. The resulting data corresponds to that reflected in FIG. 4.

Example 12

Kinetics of scFv/mRNK Binding to RBC

Ter119scFv-mRNK was prepared according to Example 5, Freshly isolated mRBCs were resuspended in PBS/BSA or previously obtained heparinated mouse plasma at equal physiological hematocrit (determined previously, ~50%) and incubated with 40 µg/ml of $^{125}$I-labeled Ter119-TM at 37° C. At the indicated time points the aliquots of the RBC suspension were taken, washed 3 times with PBS/BSA and the residual radioactivity in the pellet indicating the extent of Ter119-TM binding was determined in a γ-counter (Perkin Elmer).

Figure 6:
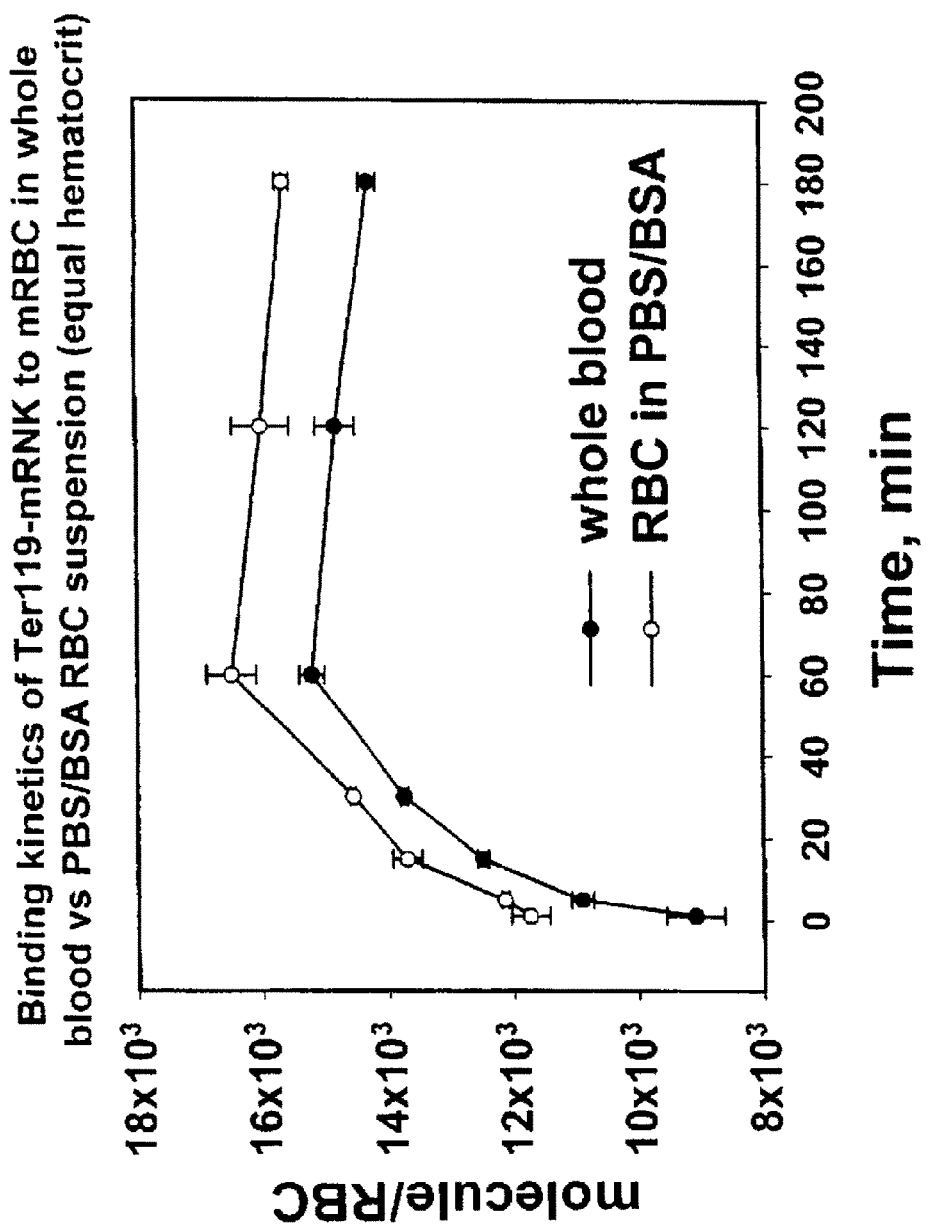
FIG. 6 illustrates the kinetics of scFv-mRNK binding to mouse heparinized whole blood and RBCs in PBS/BSA. Time to 50% saturation (molecules/RBC) is approximately 30 minutes.

Both whole and heparinized blood yielded similar binding, with a 50% saturation time of 30 minutes. Results are shown in FIG. 6.

Example 13

Biodistribution of scFv-mRNK In Vivo

A. Tracer doses (2-5 µg) of $^{125}$I radiolabeled fusion protein (prepared as indicated in Example 9) or mRNK were injected intravenously in wild type (WT) mice. One hour later, tissue uptake was determined. RBC-bound radioactivity was measured in a γ-counter (Perkin Elmer).

FIGS. 5A and 5B are bar graphs showing the biodistribution of Ter119-mRNK in vivo. Ter119-mRNK, but not mRNK, showed preferential accumulation in blood (FIG. 5A). More than 90% of Ter119-mRNK is associated with RBC at 30 min of circulation (FIG. 5B). Parallel levels of mRNK to Ter119-mRNK (FIG. 5A) within organs reflects that targeting to RBCs does not alter non-specific metabolism of the fusion.

B. Double-label tracing data was obtained parallel to the method described in section 'A' above. $^{51}$Cr labeled RBCs loaded with Ter119scFv-mRNK and RBCs loaded with Ter119scFv-mRNK-$^{125}$I were prepared. The biodistribution and percentage of RBC-bound fusion was comparable to that noted in 'A', above at one hour circulation. Similar levels of iodine and chromium isotopes in blood and of the organs reflect only minor detachment of the fusion from preloaded red blood cells (90% and 75% ID at one and three hours, respectively, of iodinated fusion in the bloodstream is associated with RBCs).

Minor reticuloendothelial system uptake of the fusion in the liver reflects a minor fraction of the fusion detached from the RBC. No uptake in the spleen was noted, reflecting no harm to RBCs. Further, no aggregation of the loaded RBCs is noted based on lack of lung clearance (within pulmonary capillaries).

Tracing of pre-loaded $^{51}$Cr-labeled complexes reflects a major fraction of injected fusion protein in viva binds to RBCs stably and rapidly, with unbound or reversibly bound material taken up by the liver parallel to untargeted mRNK.

C. Long-Term Biodistribution of Ter119 (Anti-GPA)-mRNK In Vivo

Figure 7:
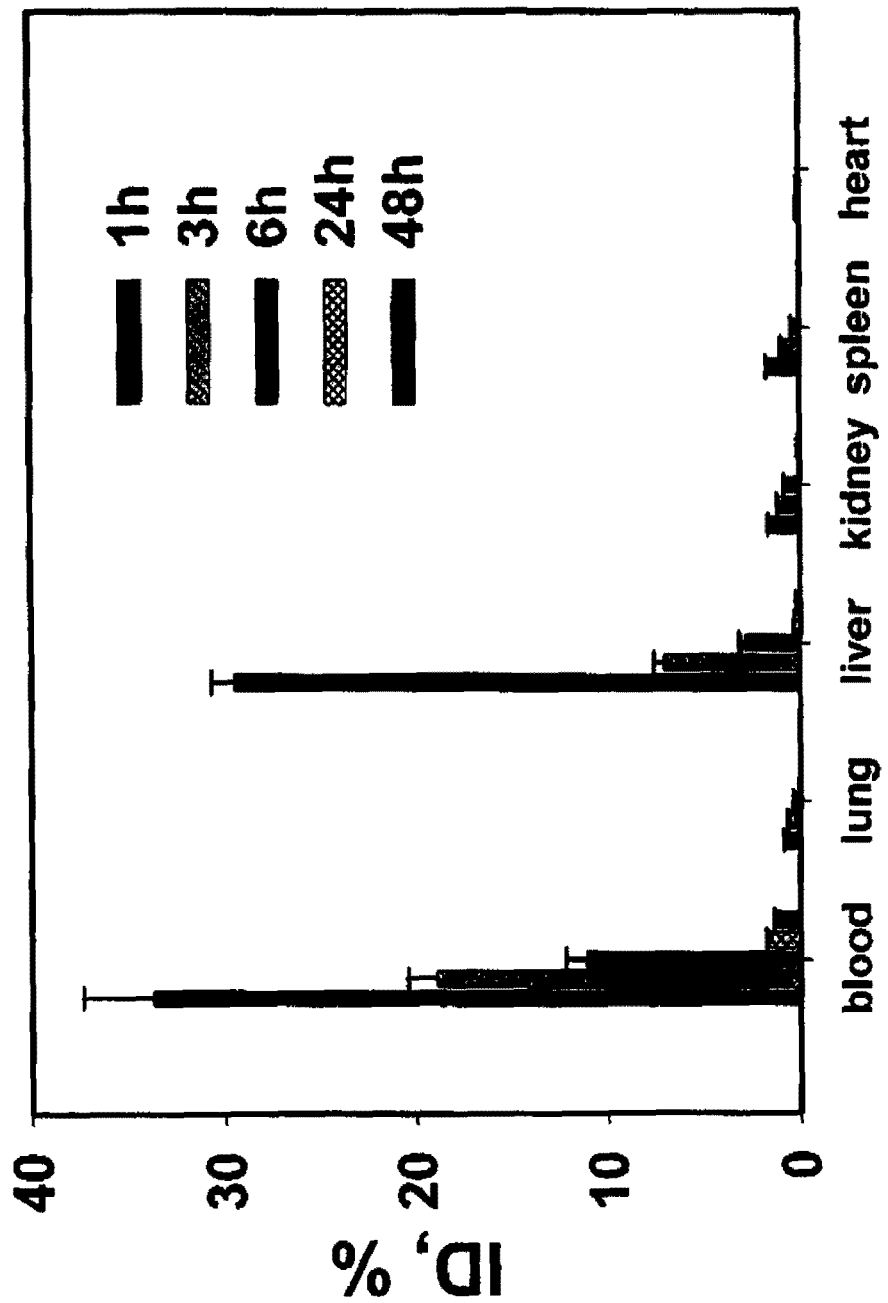
FIG. 7 reflects Ter119-mRNK-$^{125}$I distribution in organs at time points through 48 hours (left to right 1 h, 3 h, 6 h, 24 h, and 48 h).
Figure 8:
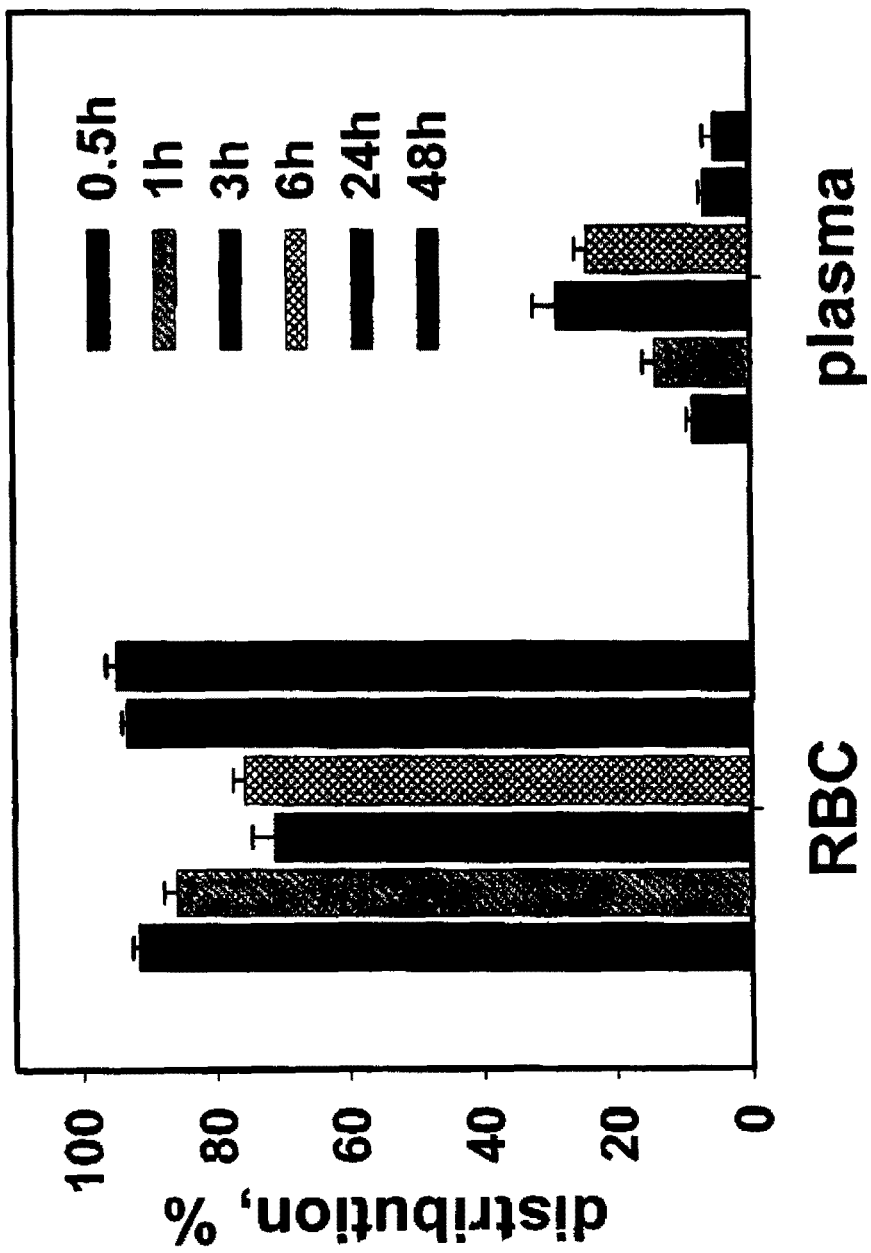
FIG. 8 reflects blood component distributions (RBC vs. plasma) at time points (left to right) 0.5 h, 1 h, 3 h, 6 h, 24 h, and 48 h, corresponding to FIG. 7.

Tracer doses (2-5 µg) of $^{125}$I radiolabeled fusion protein (prepared as indicated in Example 11) were injected intravenously in wild type (WT) mice. At time points 1 h, 3 h, 6 h, 24 h, and 48 h, tissue uptake was determined (FIG. 7). At time points 0.5 h, 1 h, 3 h, 6 h, 24 h, and 48 h, blood components distribution was determined (FIG. 8). RBC-bound radioactivity was measured in a γ-counter (Perkin Elmer).

The resulting data reflects that the fusion circulates for several hours, and that a fraction of the fusion detaches from RBC within hours after injection.

Example 14

Biodistribution of scFv-TM In Vivo

A. $^{51}$Cr labeled RBCs loaded with Ter119scFv-TM (prepared according to Example 7) and RBCs loaded with Ter119scFv-TM-$^{125}$I were prepared and injected intravenously in wild type (WT) mice. At one hour, three hours, and six hours of circulation, tissue uptake was determined. RBC-bound radioactivity was measured in a γ-counter (Perkin Elmer).

Figure 9:
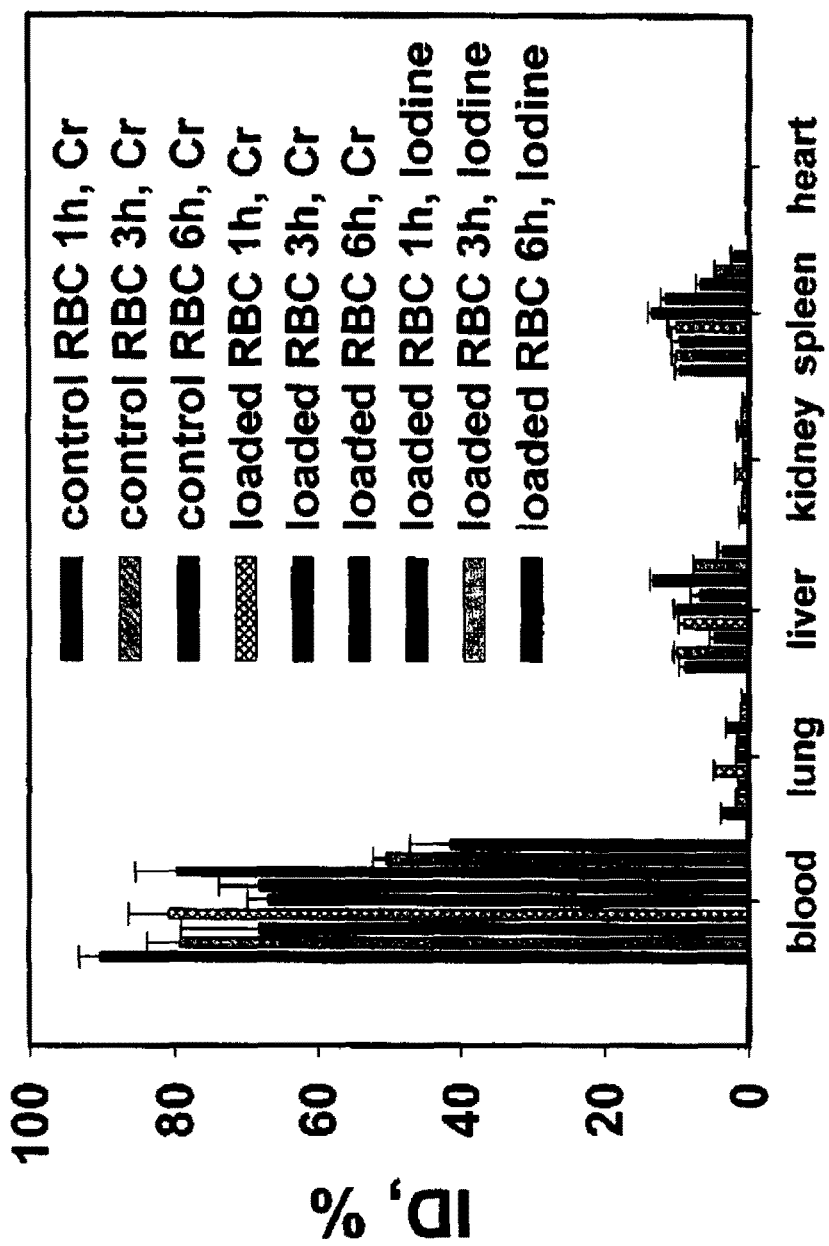
FIG. 9 shows organ distribution of Ter119-TM-$^{125}$I loaded on $^{51}$Cr-labeled mouse RBCs at 1 h, 3 h, and 6 h, or control $^{51}$Cr-labeled RBC. mouse.
Figure 10:
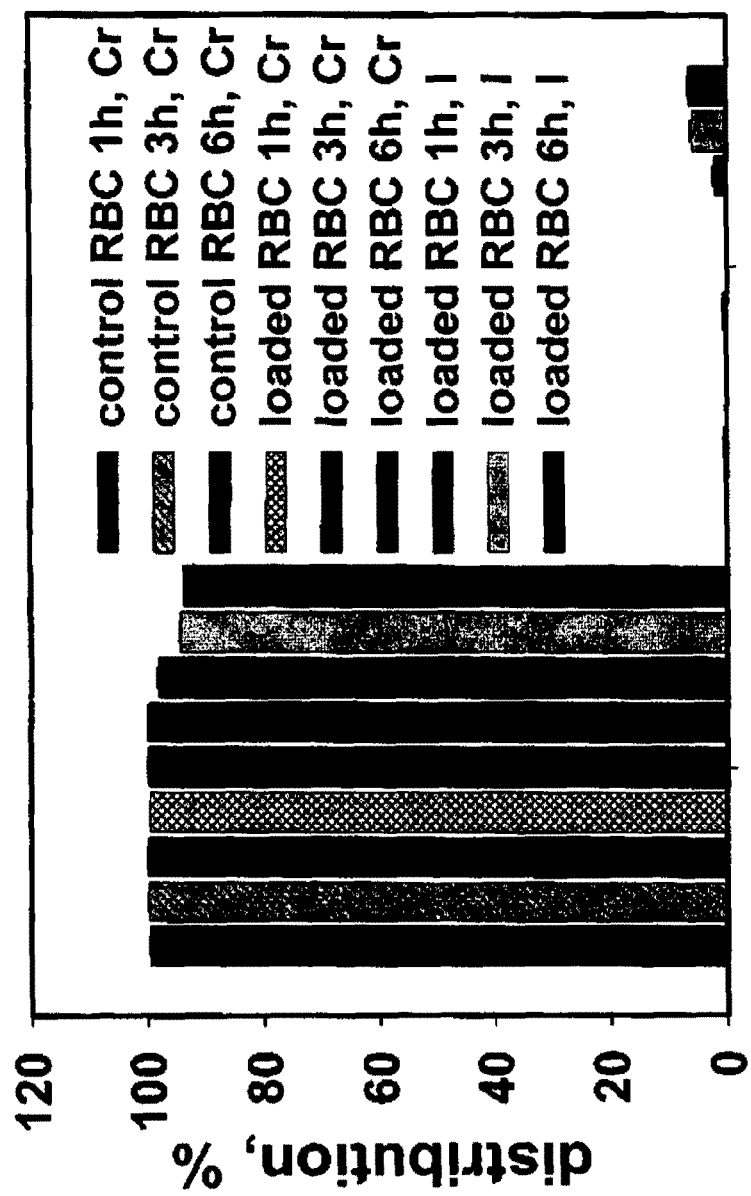
FIG. 10 reflects blood component distribution of isotopes at indicated time after injection of the complex in this experiment (RBC vs. plasma), corresponding to FIG. 9.

FIG. 9 shows a lack of accumulation of loaded RBCs in the lungs, reflecting the absence of aggregation, and lack of accumulation in the spleen reflects the absence of damage to the RBCs. FIG. 10 reflects no significant detachment of fusion from RBCs within 6 hours.

B. Long-Term Biodistribution of scFv-TM In Vivo

RBCs loaded with Ter119scFv-TM-$^{125}$I (prepared according to Example 7; see Example 9 for labeling method) were injected intravenously in wild type (WT) mice. At one-half hour, one hour, three hours, six hours, and twenty-four hours of circulation, tissue uptake was determined. RBC-bound radioactivity was measured in a γ-counter (Perkin Elmer).

Figure 11:
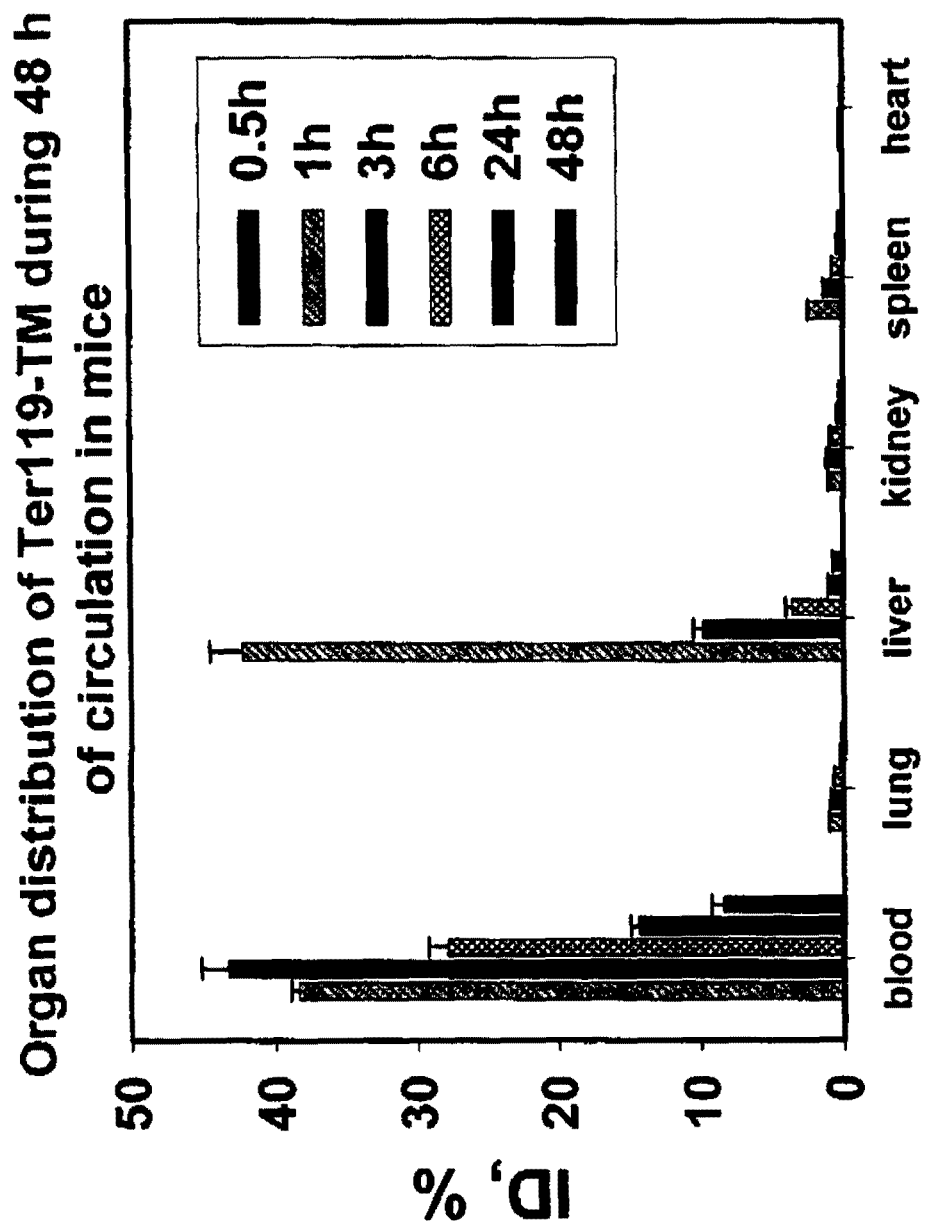
FIG. 11 reflects Ter119-TM-$^{125}$I distribution in organs at time points through 48 hours (left to right 0.5 h (no sample taken), 1 h, 3 h, 6 h, 24 h, and 48 h).
Figure 12:
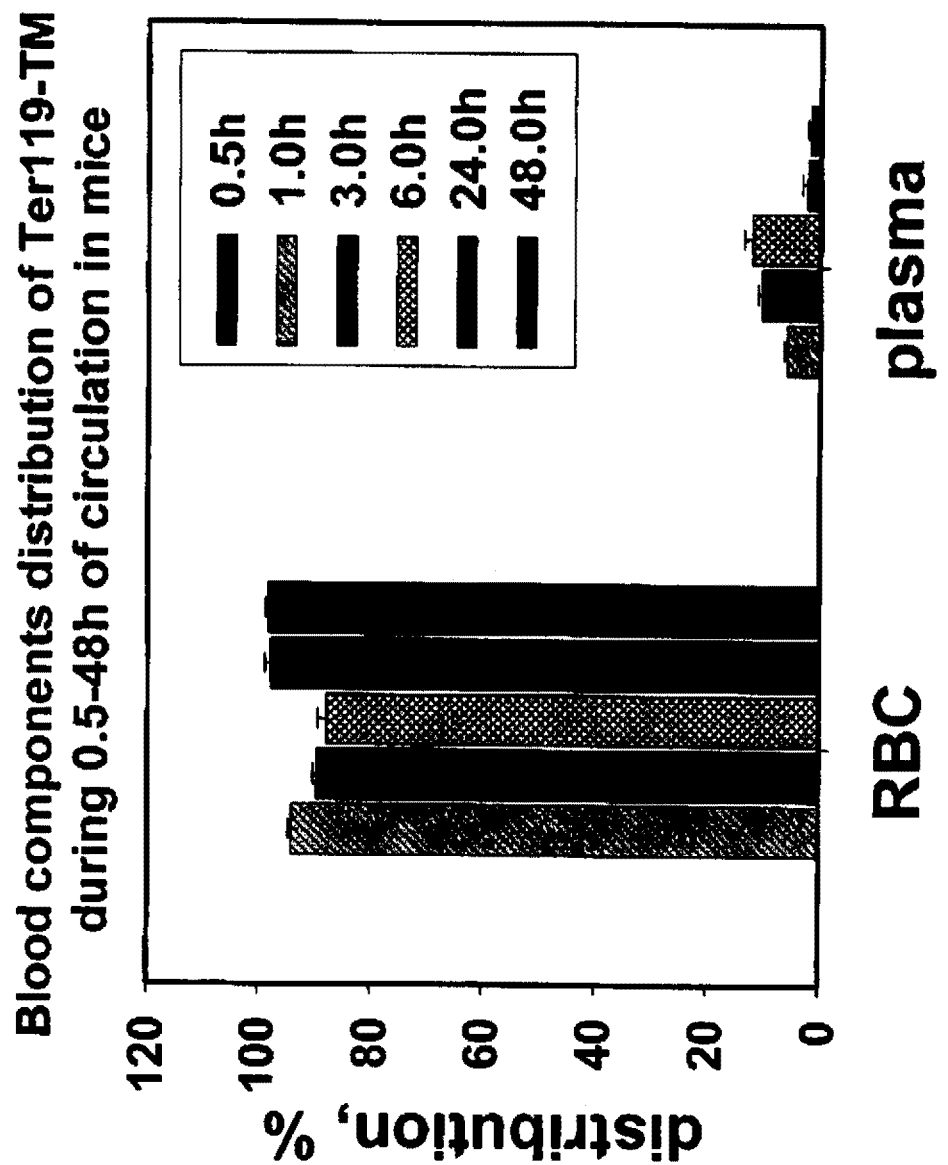
FIG. 12 reflects blood component distributions (RBC vs. plasma) at time points (left to right) 0.5 h, 1 h, 3 h, 6 h, 24 h, and 48 h, corresponding to FIG. 11.

FIG. 11 shows a lack of accumulation of loaded RBCs in the lungs, reflecting the absence of aggregation, and lack of accumulation in the spleen reflects the absence of damage to the RBCs. FIG. 12 reflects no significant detachment of fusion from RBCS within 6 hours.

C. Stable and Prolonged Loading Via Intraperitoneal Delivery

RBCs loaded with Ter119scFv-TM-$^{125}$I (prepared according to Example 7) were injected intraperitoneal (IP) in wild type (WT) mice. At one hour and three hours of circulation, tissue uptake was determined. RBC-bound radioactivity was measured in a γ-counter (Perkin Elmer).

Figure 13:
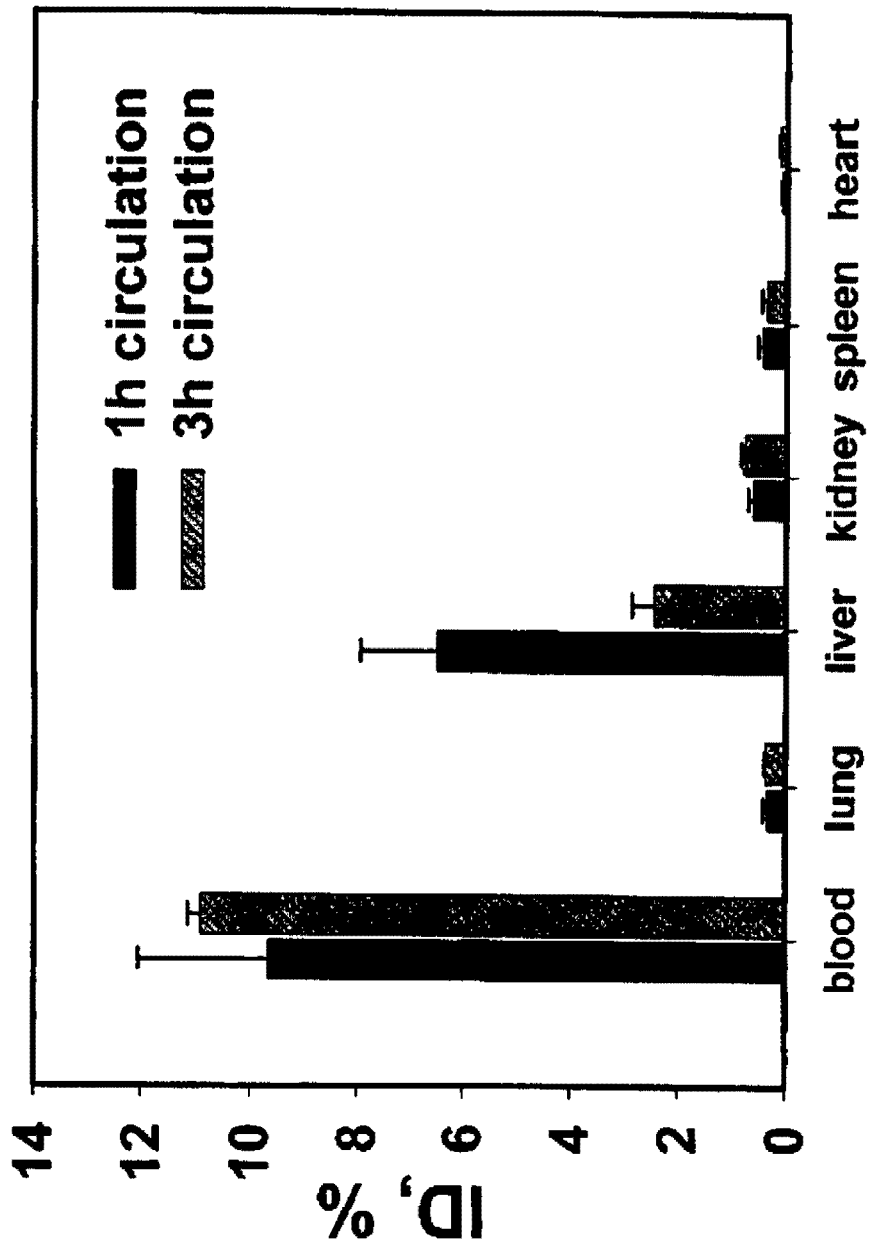
FIG. 13 reflects Ter119-TM-$^{125}$I distribution in organs, when delivered by intraperitoneal (IP) injection, at time points 1 h and 3 h.
Figure 14:
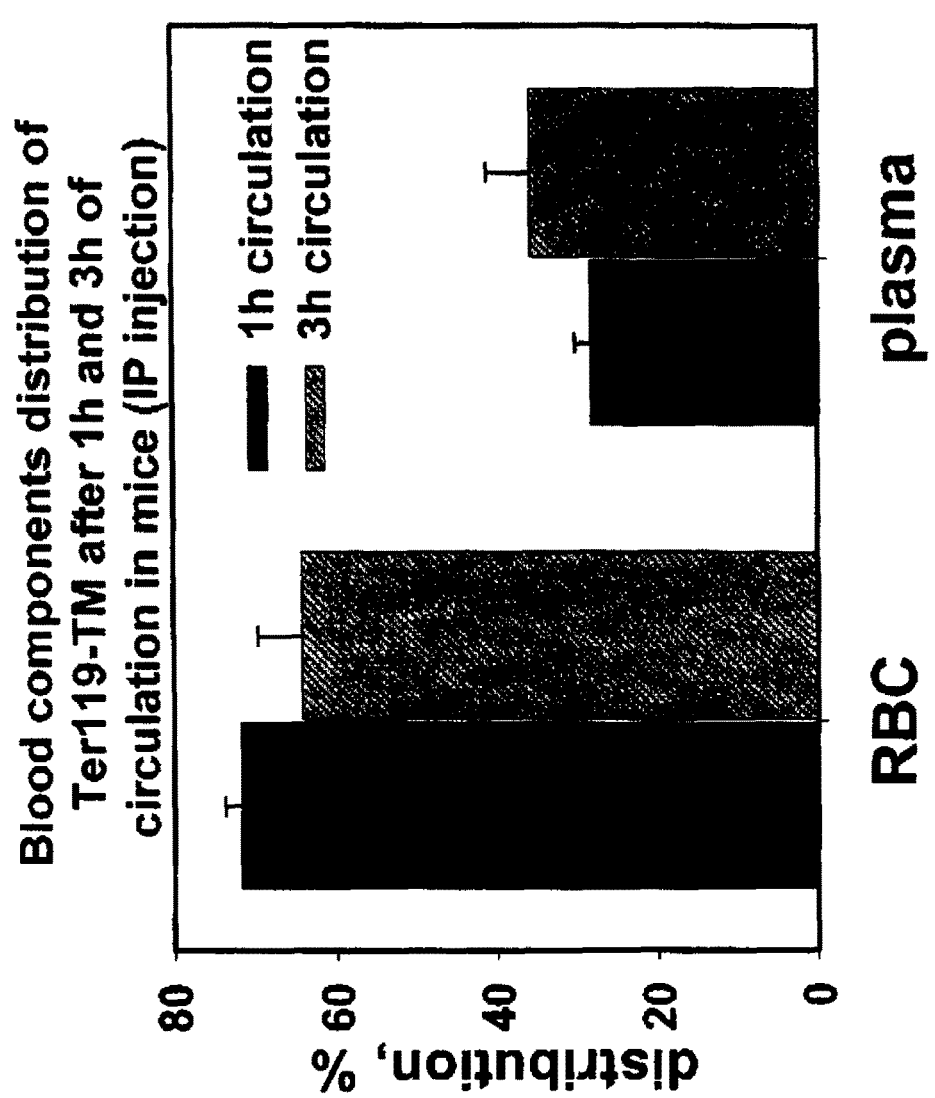
FIG. 14 reflects blood component distribution of injected isotopes in this experiment (RBC vs. plasma) at time points 1 h and 3 h, corresponding to FIG. 13.

FIGS. 13 and 14 reflect that intraperitoneal (IP) delivery offers stable and prolonged loading of RBCs. IP delivery provides for chronic and repetitive use.

Example 15

Biodistribution of scFv-uPA-T In Vivo

A. $^{51}$Cr labeled RBCs loaded with Ter119scFv-uPA-T (prepared according to Example 4) were prepared and injected intravenously in wild type (WT) mice. At one hour, three hours and six hours of circulation, tissue uptake was determined. RBC-bound radioactivity was measured in a γ-counter (Perkin Elmer).

The resulting data shows a lack of accumulation of loaded RBCs in the lungs, reflecting the absence of aggregation, and lack of accumulation in the spleen reflects the absence of damage to the RBCs. The data also reflects that there was no significant detachment of fusion from RBCs within 6 hours.

B. Long-Term Biodistribution of Ter119-uPA-T (lUK-T) In Vivo

RBCs loaded with Ter119scFv-uPA-T-$^{125}$I (see Example 9 for labeling method) were injected intravenously in wild type (WT) mice. At time points through 48 hours of circulation, tissue uptake was determined. RBC-bound radioactivity was measured in a γ-counter (Perkin Elmer).

Figure 15:
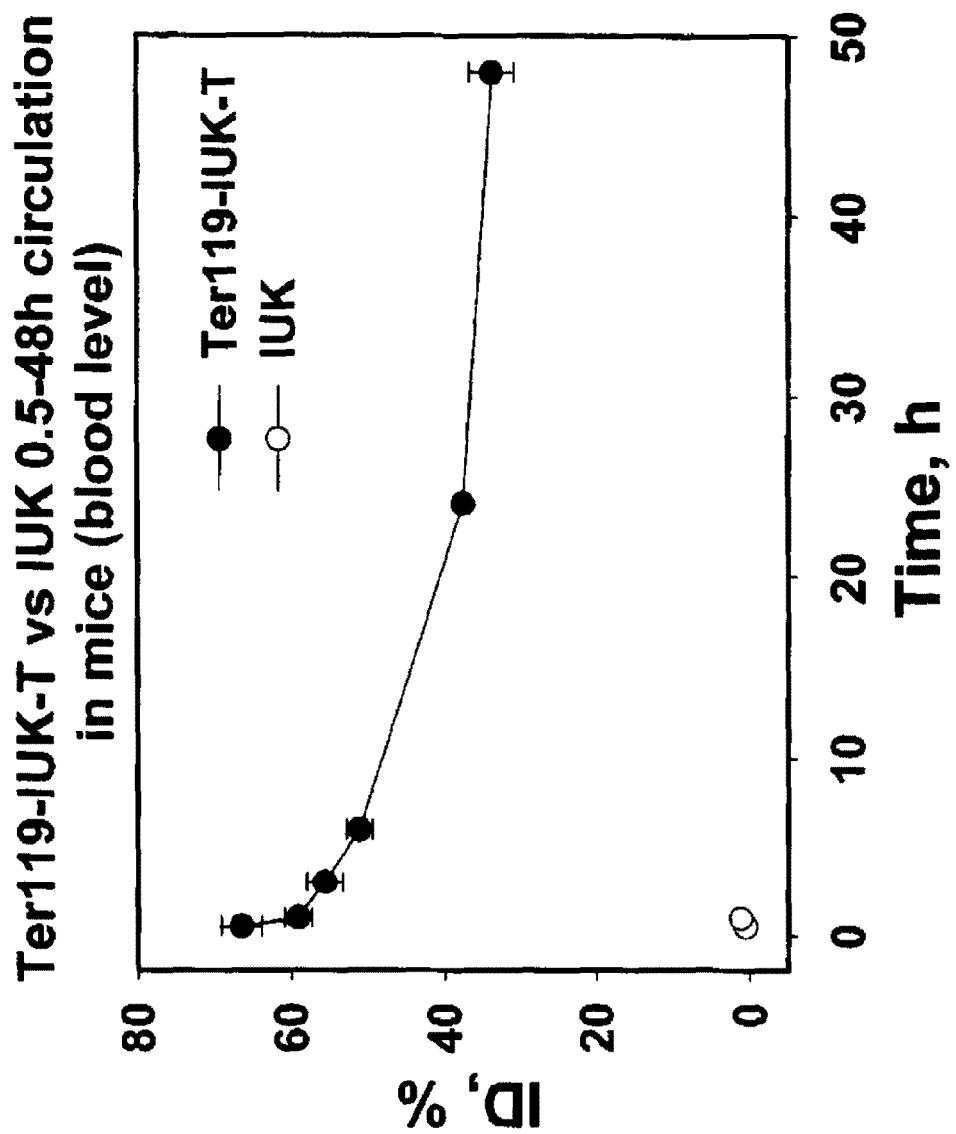
FIG. 15 shows circulation of the fusion protein Ter119-lUK-T (vs. free uPA (lUK)) in blood during the 48 hours after injection.
Figure 16:
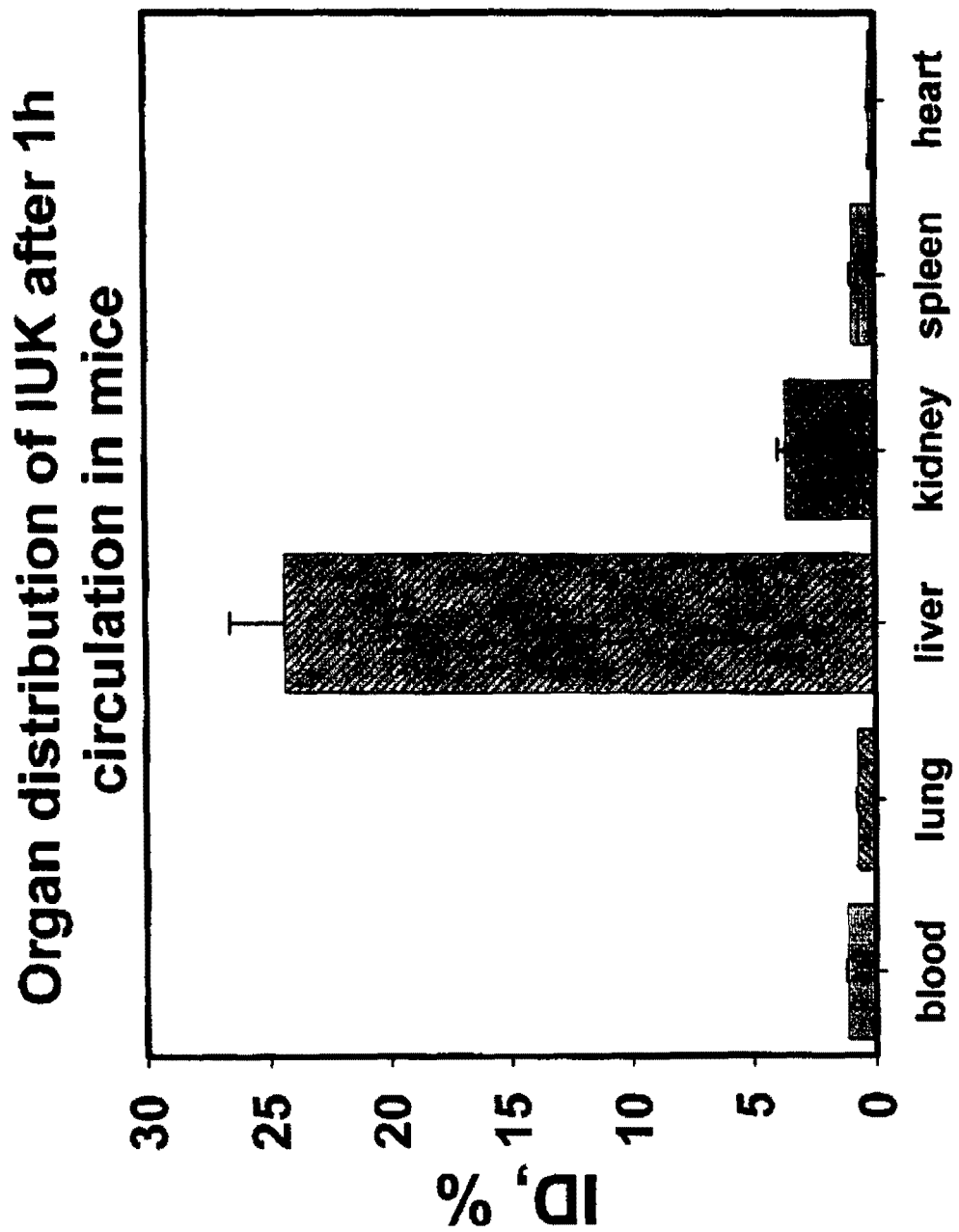
FIG. 16 reflects organ distribution of free uPA (lUK) after one hour of circulation.
Figure 17:
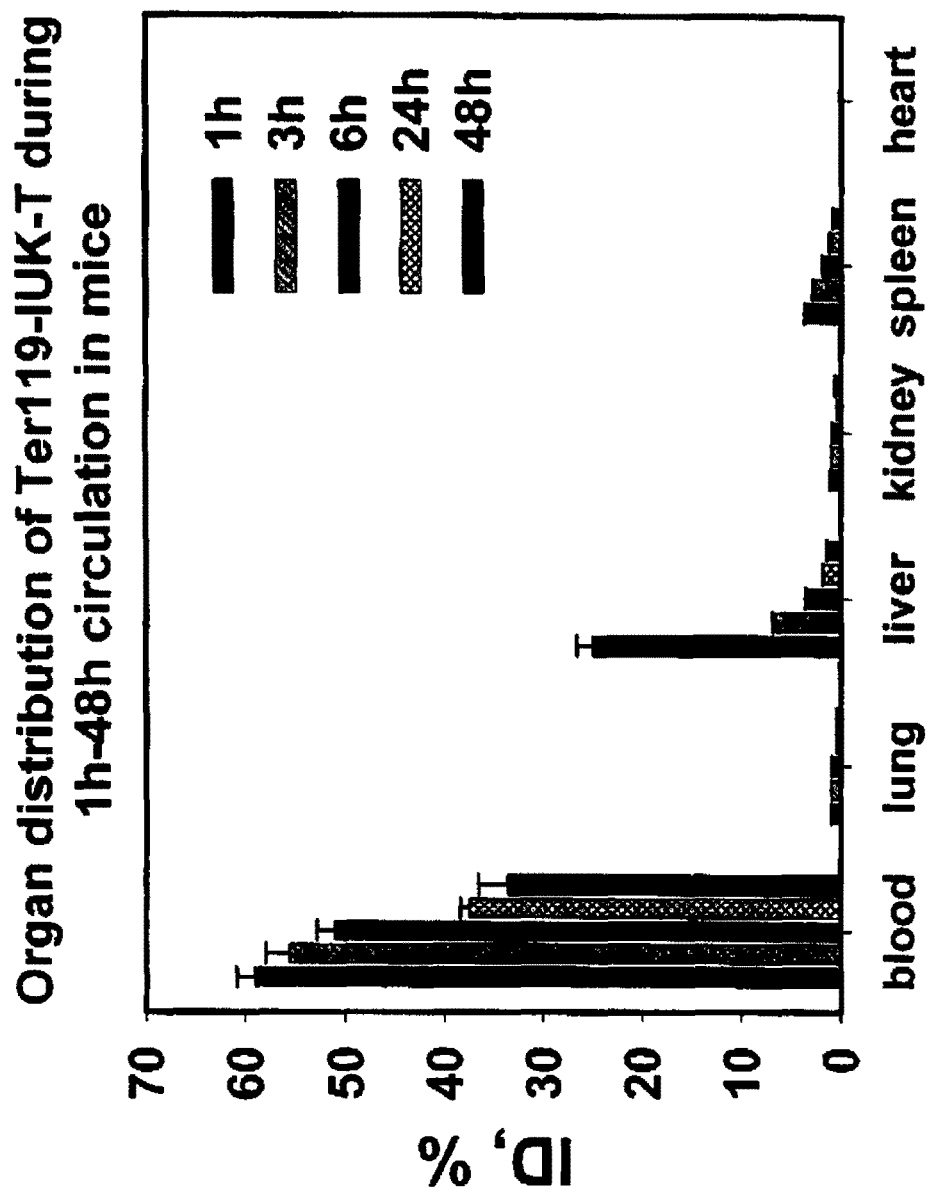
FIG. 17 reflects organ distribution of the fusion protein (Ter119-lUK-T) through 48 hours (left to right, 1 h-48 h) after injection.
Figure 18:
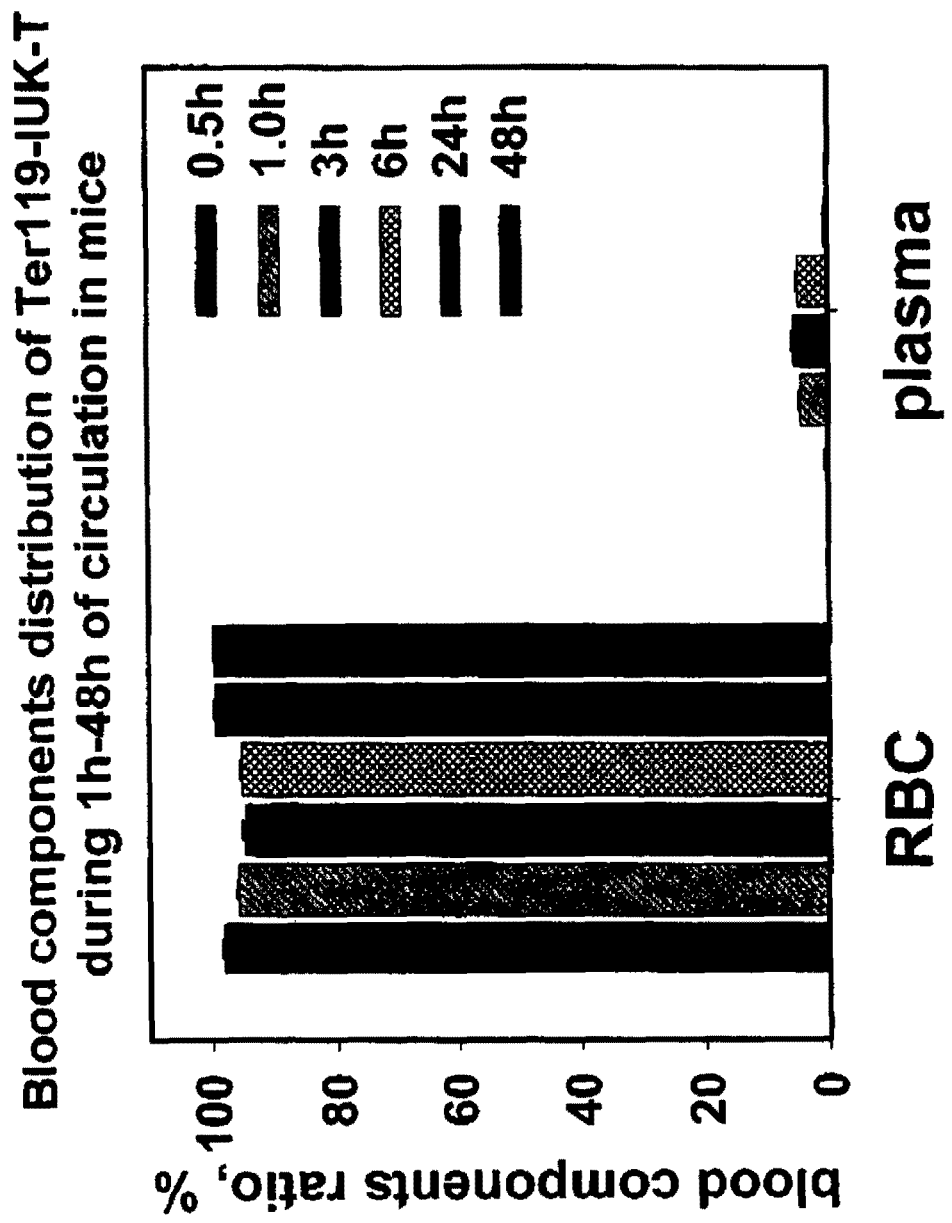
FIG. 18 reflects the distribution of the fusion protein (Ter119-lUK-T) between blood plasma and cells through 48 hours (left to right, 0.5 h-48 h) after injection.

FIG. 15 shows circulation of the fusion protein in blood during the 48 hours after injection. FIGS. 16 and 17 reflect organ distribution of free uPA (lUK) and the fusion through 48 hours after injection. FIG. 18 reflects the distribution of the fusion protein between blood plasma and cells through 48 hours after injection. Non-targeted protein is lUK (uPA).

The Ter119scFv-uPA fusion bound to RBCs circulates longer than the scFv-mRNK fusion bound to RBCs. While not wishing to be bound by theory, one rational for this difference may be higher affinity of the uPA fusion due to protein folding (enhanced binding properties). Another rational is that given the RBC-bound scFv-uPA-T pro-drug does not bind PAI-1 and other inhibitors until thrombin releases uPA from the fusion. PAI-1, which is known to accelerate clearance of plasminogen activators from blood via hepatic receptors, may more rapidly clear the constitutively active Ter119scFv-mRNK fusion.

Example 16

Fibrin Clot Lysis by Mouse and Human Loaded Red Blood Cells

Fusion proteins were prepared comprising an anti-glycophorin A associated protein (mouse RBC) scFv derived from parental rat mAb Ter119 as described in Example 4, and kringle 2 and protease domains of mouse tPA. Moreover, the protease domain contains point mutations similar to those in human tenectase making it more resistant to inhibition by PAI-1.

Figure 3:
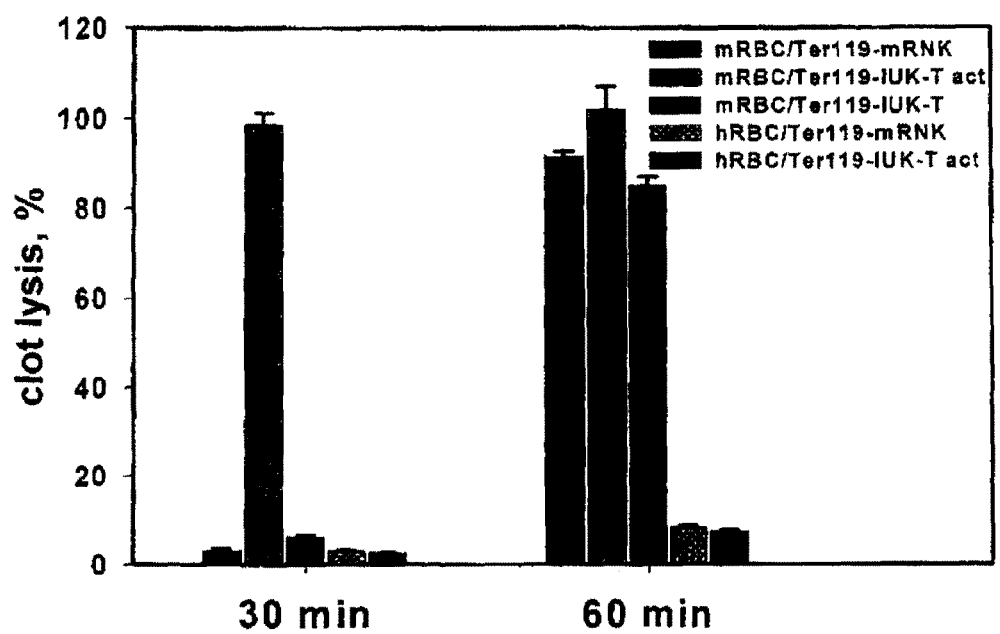
FIG. 3 is a bar graph showing fibrin clot lysis by mouse and human RBC loaded with Ter119-lmvUK-T and Ter119-mRNK. This fusion protein comprises an anti-glycophorin A associated protein (mouse RBC) scFv derived from parental rat MAb Ter119 as described in FIG. 1, and kringle 2 and protease domains of mouse tPA. Moreover, the protease domain contains point mutations similar to those in human Tenectase making it less sensitive to inhibition by PAI-1. The bars are labeled as shown in the figure. Mouse and human RBCs were incubated in serum free medium from induced S2 cells transfected with a plasmid encoding either Ter119-lmvUK-T (indicated in the figure as Ter119-IUK-T) or Ter119-mRNK. RBC were washed and incorporated into fibrin solution before induction of clotting by addition of Ca and thrombin. Part of RBC loaded with Ter119-lmvUK-T were pre-incubated with thrombin in order to activate fusion protein. The experiment confirmed the high selectivity of binding of both fusion proteins to mouse RBC vs human RBC and their proteolytic activity in mRBC surface bound state. Moreover, it showed that pre-incubation with thrombin accelerates subsequent dissolution of thrombi by mRBC-bound Ter119-lmvUK-T, yet even short time exposure of Ter119-lmvUK-T to thrombin during clotting is enough to activate the fusion protein.

A. Mouse and human RBCs were incubated in serum free medium from induced *Drosophila* S2 cells transfected with a plasmid encoding either Ter119-lmwUK-T (prepared according to Example 4) or Ter119-mRNK (SEQ ID NO: 8)(prepared according to Example 5). RBCs were washed and incorporated into fibrin solution before induction of clotting by addition of calcium and thrombin. RBCs loaded with Ter119-lmvUK-T were pre-incubated with thrombin in order to activate the fusion protein. The experiment confirmed the high selectivity of binding of both fusion proteins to mouse RBC vs. human RBC and their proteolytic activity in the RBC surface bound state (FIG. 3). Moreover, it showed that even short time exposure of Ter119-lmwUK-T to thrombin during clotting is enough to activate the fusion protein. Human and mouse RBC loaded with either Ter119-lmvUK-T (activated (act) and non-activated) or Ter119-mRNK were injected into preformed fibrin clots (10 µl of 50% Hc RBC suspension). Again, only mRBC caused lysis and in the case of Ter119-lmwUK-T the necessity of thrombin activation of fusion protein was confirmed (FIG. 3).

B. Mouse RBCs were incubated in serum free medium from induced *Drosophila* S2 cells transfected with a plasmid encoding scFv-uPA-T (prepared according to Example 4). RBCs were washed, pre-incubated with thrombin in order to activate the fusion protein, washed, and incorporated into fibrin solution. Clotting was induced by addition of calcium and thrombin, and allowed to incubate for 5 or 24 hours.

Figure 19:
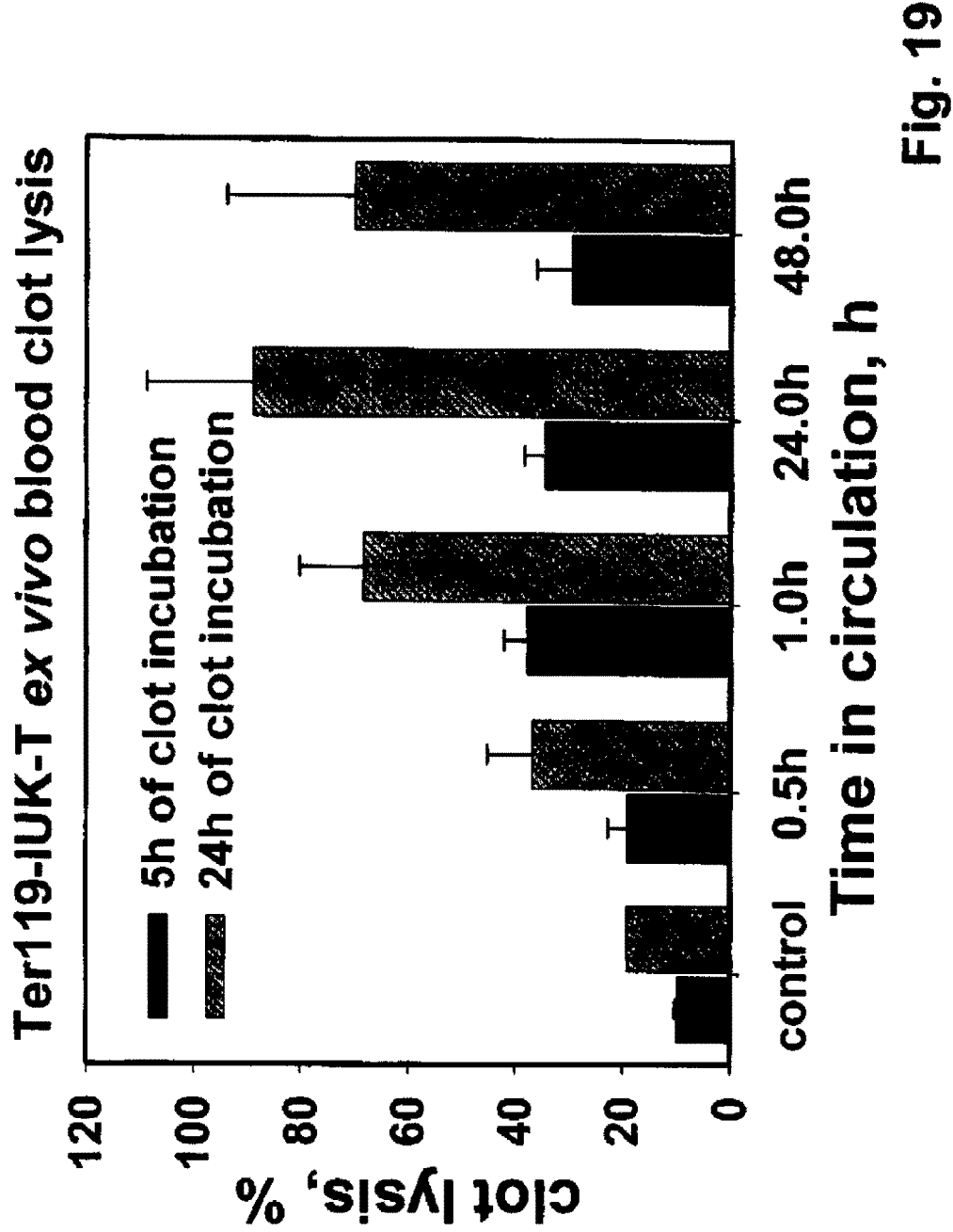
FIG. 19 reflects clot lysis (as a percentage) by fusion protein Ter119-lUK-T through 48 hours circulation after clot incubation (5 h or 24 h). Maximal fibrinolytic effect was noted from hour 1 through 48 hours after injection into the fibrin clot.

FIG. 19 reflects clot lysis through 48 hours after clot incubation. Maximal fibrinolytic effect was noted from hour 1 through 24 hours after injection into the fibrin clot. Based on these results, the construct is suited to prolonged thromboprophylaxis.

Example 17

Kinetics of Fibrin Clot Lysis by scFv-mRNK Dose

Figure 20:
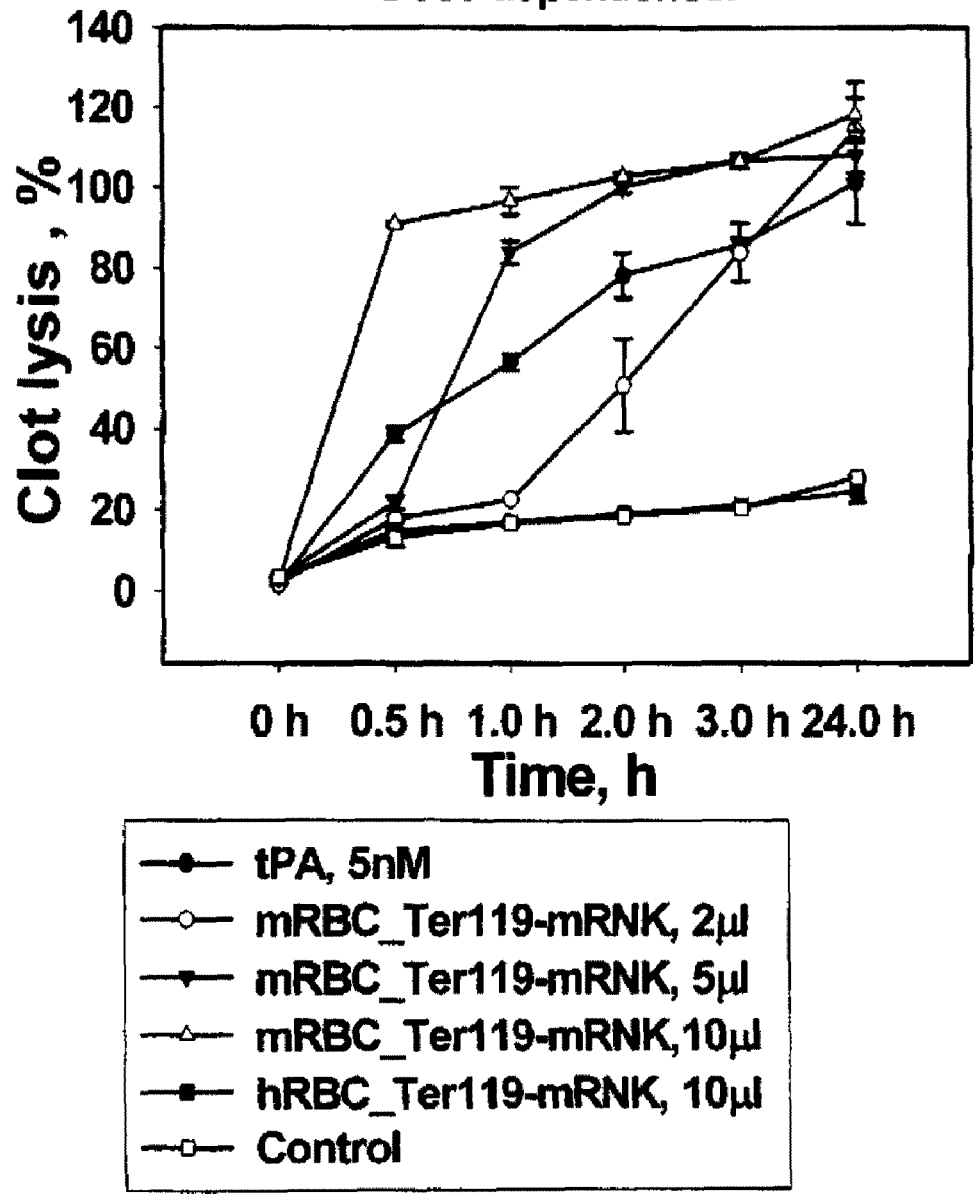
FIG. 20 shows in vitro fibrin clot lysis by 2 µL, 5 µL, and 10 µL of mRBCs loaded with Ter119-mRNK at 17,000 mol/RBC (dose dependence on clot lysis % vs time following injection). Human (h)RBC-Ter119-mRNK matches negative control, as Ter119 is specific for mouse RBCs. tPA is provided as a positive control.

Ter119 scFv-mRNK was prepared according to Example 5. mRBCs were loaded to 17,000 mol/RBC, and RBCs were washed to remove unbound fusion. 2, 5, and 10 µL of 50% RBC suspension were added to a fibrinogen solution prior to clotting. The resulting RBC bound mRNK concentrations were 1.5 nM, 3.74 nM, and 7.48 nM, respectively. Resulting 50% fibrinolysis time was 130, 45, and 15 minutes, respectively, which is similar to 60 minutes obtained with 5 nM tPA (positive control). FIG. 20 reflects these results in graphical form.

Example 18

Ex Vivo Fibrinolysis by Injected scFv-mRNK

Ter119scFv-mRNK was prepared according to Example 5. PBS (control), non-targeted mRNK, or the fusion was injected into mice via jugular vein at equimolar doses. Blood was collected from animals 45 minutes post-injection (without anticoagulant), and blood clots were formed with addition of tracer dose of radioactive fibrinogen. Clots were matured for 20 minutes, covered with PBS, and brought to 37° C. Probes of supernatants were used to detect radioactivity, which indicated dissolution of blood clots.

Figure 21:
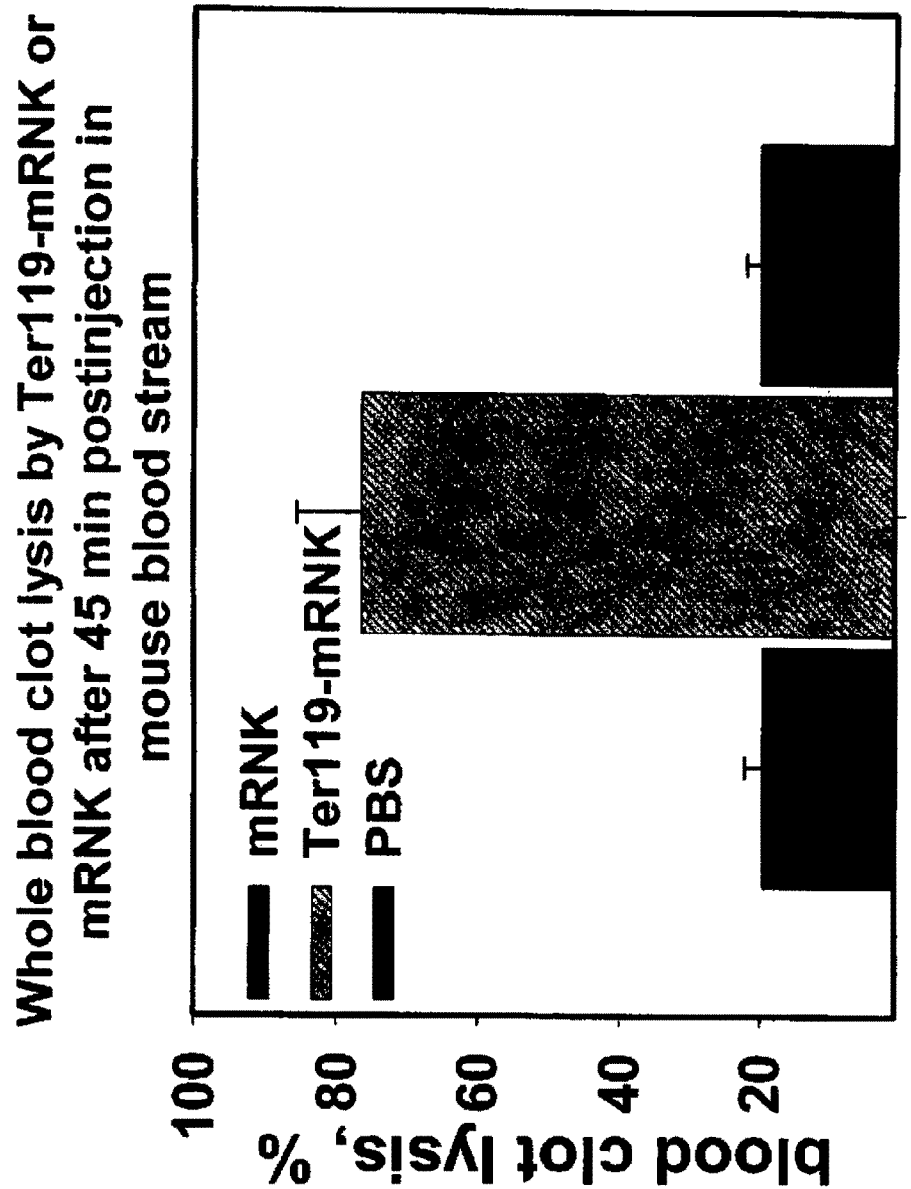
FIG. 21 illustrates that following 45 minutes circulation, scFv-mRNK retains its ability to activate plasminogen reflected by lysis of clots formed from blood obtained from mice injected with seFv-mRNK (radioactive fibrinogen used as tracer). Free mRNK matches negative control (PBS), as anticipated.

The resulting data reflects that following 45 minutes circulation, the scFv-mRNK retains its ability to activate plasminogen, which was reflected by clot lysis. FIG. 21 reflects the results in graphical form. RBC-bound scFv-mRNK is functionally active for significantly longer than non-targeted mRNK.

Example 19

Kinetics of scFv-uPA-T Activation (Cleavage) by Thrombin

Figure 22:
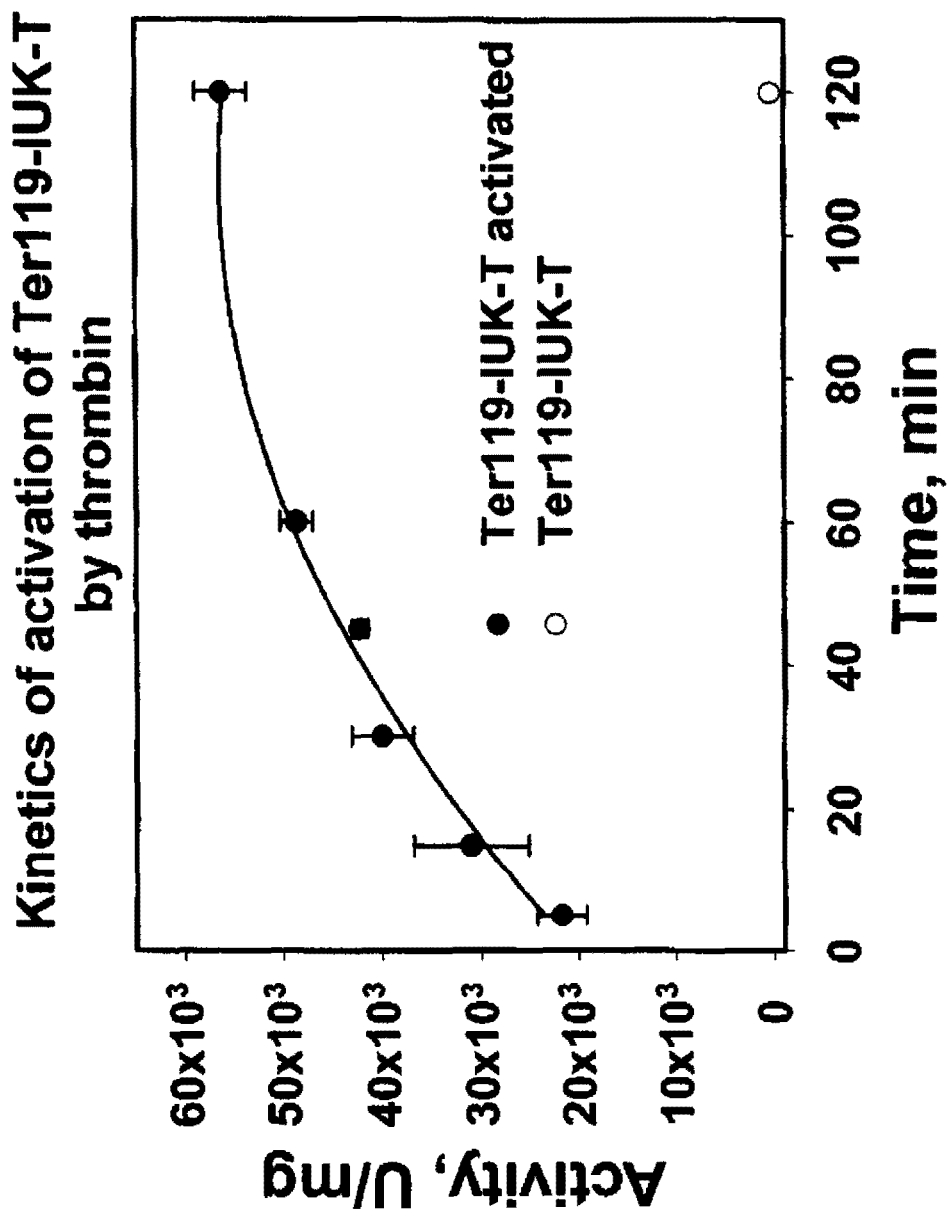
FIG. 22 reflects kinetic data (activity (U/mg) as a function of time) of the activation of Ter119-lUK-T (Ter119scFv-uPA-T) by thrombin.

Ter119scFv-uPA-T was prepared according to Example 4.
A. Anti-GPA-scFv/uPA-T (Ter119-IUK-T) was brought to final concentration of 150 nM in PBS containing $Ca^{2+}$ and incubated with 25 μM thrombin for indicated times in order to test the kinetic of anti-GPA-scFv/uPA-T activation (conversion into 2 chain form). At the indicated time points the reaction was stopped by addition of hirudin (final concentration in the assay 33 U/ml). The activity of anti-GPA-scFv/uPA-T was tested by Spectrozyme-uPA Kit (American diagnostica) as per manufacturer. The results are reflected in FIG. 22.

Figure 23:
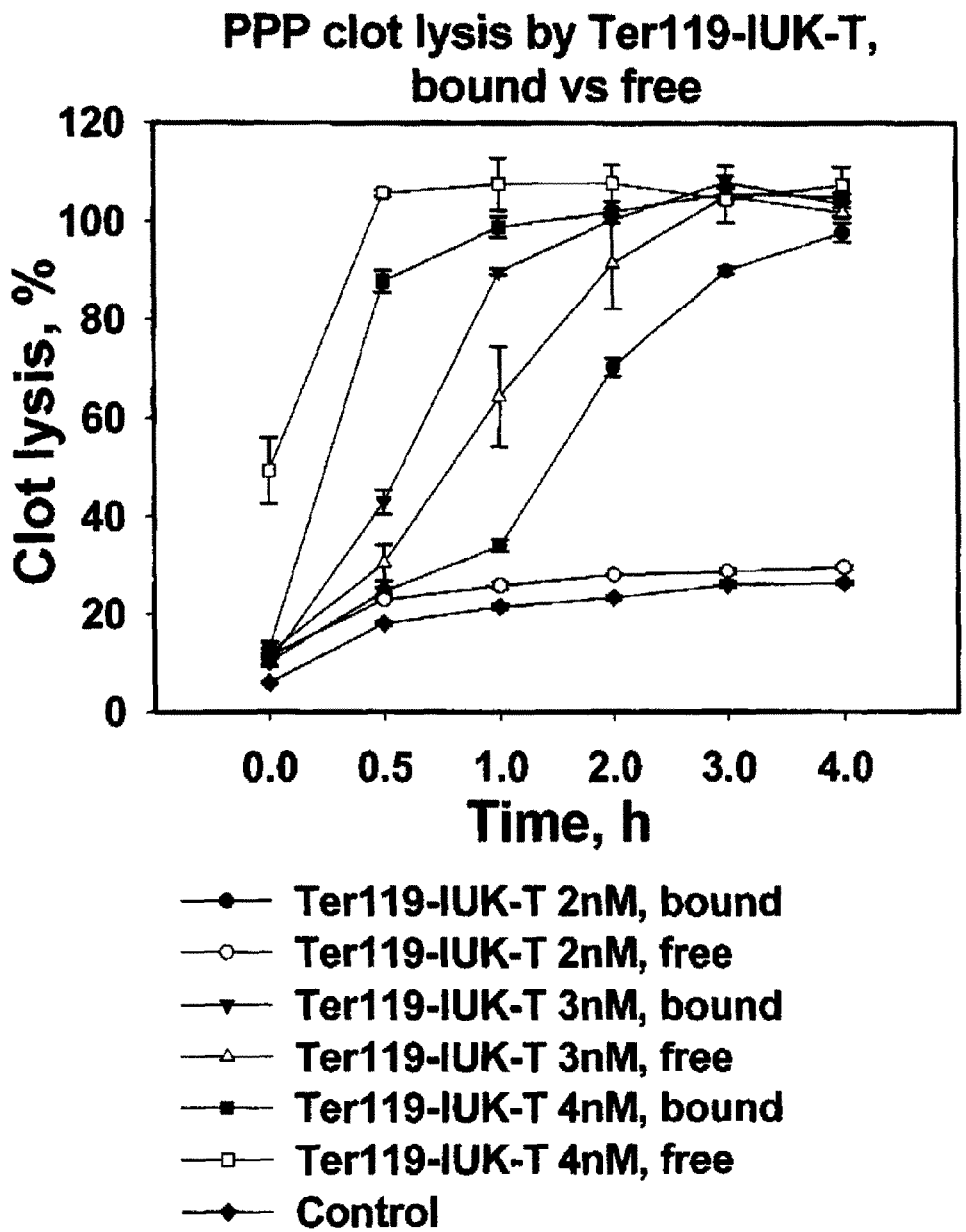
FIG. 23 shows clot lysis in human platelet poor plasma by Ter119-lUK-T (bound to mouse RBC vs. free), as a function of concentration and time. Near rate limiting doses are utilized to explore effects of binding to RBC on activity of the fusion.

B. Using the protocol of 'A', above, near rate-limiting doses of scFv-uPA-T RBC-bound fusion (2-4 nM), the RBC-bound fusion caused significantly faster and more effective fibrinolysis of clots formed from human platelet poor plasma (PPP), as reflected in FIG. 23. Without wishing to be bound by theory, it is believed that this effect is due to the masking of plasma inhibitors including PAI-1 by the RBC glycocalyx. Further, as reflected in FIG. 23, at concentrations exceeding PAI-1's capacity to inhibit plasminogen activators via irreversible binding, the free fusion was slightly more effective than RBC-bound fusion. This is believed to be due to a less impeded diffusion into the fibrin network.

Example 20

In Vivo Thrombolysis in a Model of Intravascular Thrombolysis in Mice-scFv-uPA-T The method of dissolution of carotid arterial thrombi according to J. Murciano, Nature Biotechnology, 21(8): 891-896, 895 (August 2003) was used. Ter119scFv-uPA-T fusion (prepared according to Example 4), PBS, and uPA (equimolar) were administered via injection via jugular vein. 30 minutes after administration, acute vascular trauma is induced by administration of 15% $FeCl_3$ (2 minutes flow).

Injection of non-targeted uPA did not affect rapid thrombotic occlusion of the artery comparing with mice pre-treated with placebo (PBS). On average, in animals from PBS or uPA, a complete arterial occlusion occurred within ten minutes of vessel damage and no significant reperfusion occurred in the ensuing 45 minutes after insult. In contrast, pre-injection of the fusion provided either complete prevention of occlusion, or rapid reperfusion after a brief period of intermittent reduction of perfusion.

These data indicate that the scFv-uPA-T fusion provides thromboprophylaxis in animal models.

Example 21

In Vivo Thrombolysis in a Model of Intravascular Thrombolysis in Mice-scFv-mRNK

The method of dissolution of carotid arterial thrombi according to J. Murciano, et al., Nature Biotechnology, 21(8): 891-896, 895 (August 2003) was used. Ter119scFv-mRNK fusion (prepared according to Example 5), PBS, and mRNK (equimolar—4 mg/kg scFv/mRNK vs. 2 mg/kg mRNK) were administered via injection via jugular vein. 30 minutes after administration, acute vascular trauma is induced by administration of 15% $FeCl_3$ (2 minutes flow).

Injection of non-targeted RNK did not affect rapid thrombotic occlusion of the artery comparing with mice pre-treated with placebo (PBS). mRNK did not attenuate nor delay artery occlusion (defined as complete cessation of blood perfusion by Doppler ultrasound). However, the equimolar dose of scFv-mRNK fusion significantly delayed occlusion (~11 minutes vs. ~6 minutes)

Figure 24:
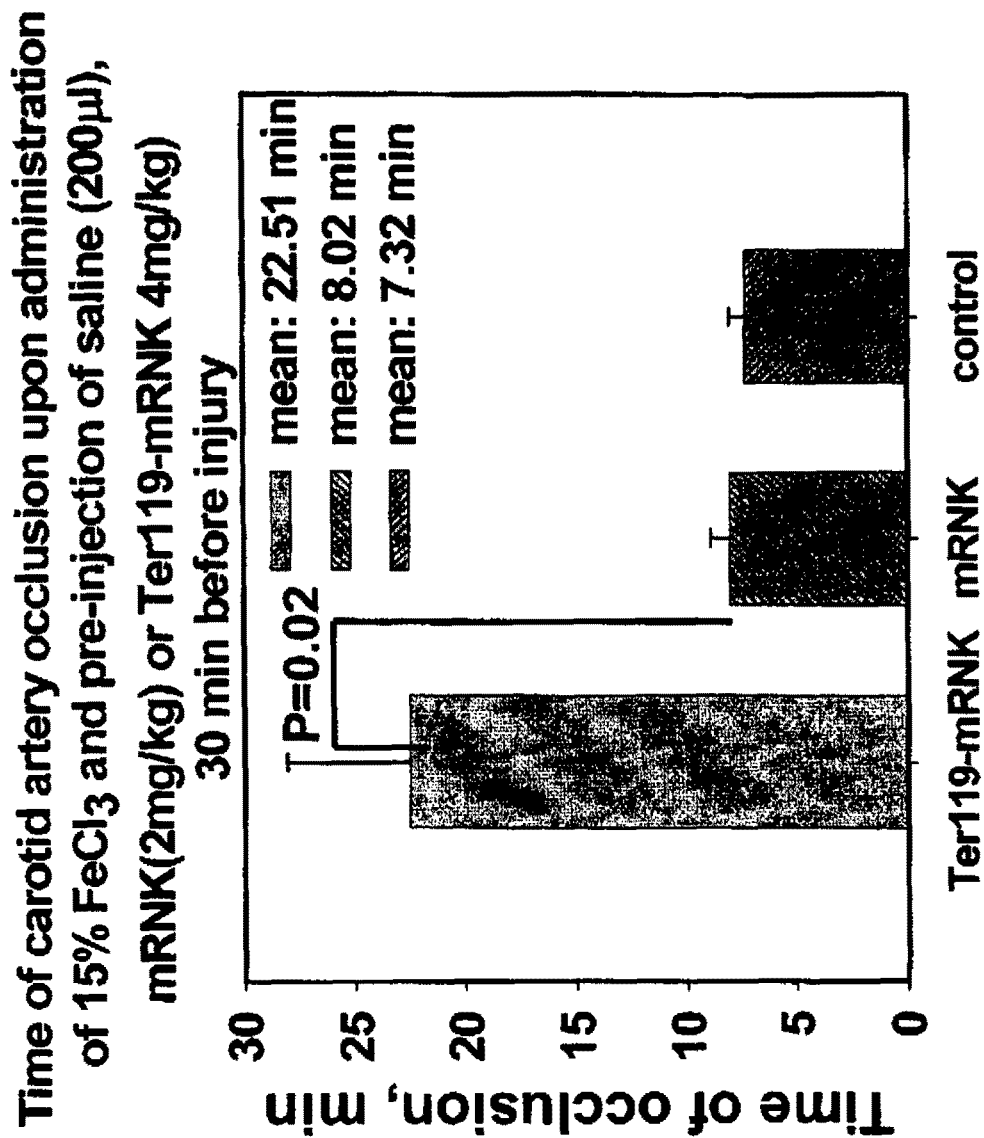
FIG. 24 shows the thromboprophylactic effect of Ter119scFv-mRNK manifested by delayed full occlusion. Free RNK was comparable to PBS negative control, as expected.

The data (FIG. 24) indicates that the scFv-mRNK fusion provides thromboprophylaxis in animal models.

Example 22

Prophylactic Thrombolysis of Cerebrovascular Thrombi

The protocol of K. Danielyan, et al. J. Pharm. and Exp. Therapeutics, 321(3): 947-952, 948 (June 2007) is used.

Ter119scFv-mRNK fusion (prepared according to Example 5), mRNK alone (equimolar), and PBS, are administered in a standard 120-4, volume of PBS via catheter inserted into the right femoral vein of anesthetized mice. 30 minutes after administration, a suspension of $^{125}$I-fibrin emboli is injected via the right middle cerebral artery. 30 minutes later, mice are sacrificed and $^{125}$I content of the brain are measured to determine the extent of cerebrovascular thrombolysis based on the amount of residually radiolabeled clots residing in the brain.

Residual activity for scFv-mRNK fusion mice is anticipated to be significantly lower than that for PBS mice alone. scFv-mRNK fusion is thus anticipated to provide thromboprophylaxis of cerebrovascular thrombi in animal models.

Example 23

Binding of scFv-mRNK Fusion to Glycophorin A

A. Generation of Human Anti-Glycophorin A (hGPA) scFv
The scFv with specificity for hGPA is generated essentially as described (Spitzer, et al., Mol. Immunol., 40:911-919 (2004)) from the mouse hybridoma cell line BRIC 256 (Anstee, et al, Eur. J. Immunol., 12:228-232 (1982). This line secretes an IhG1 mAb that recognizes a blood group-independent epitope on human GPA (Gardner, et al, Immunology, 68:283-289 (1989)). Total RNA is isolated (RNeasy™; Qiagen). Reverse transcription, followed by PCR (RT-PCR), is conducted using the SMART™ technology (BD Clontech) using primer combinations described previously (Dubel, et al., J. Immunol. Methods, 175:89-95 (1994). The resulting H and L chain variable cDNA fragments are subclosed into pCR2.1-TOPO (Invitrogen Life Technologies). After introducing suitable flanking restriction sites via PCR, the $V_H$ and $V_L$ chains are combined with a $(G_4S)_3$ linker resulting in the scFv Bric-256. Analysis of the amino acid primary sequence to determine the complemetarity determining regions of the scFv Bric-256 is performed by applying the rules described at Ab Structure and Sequence Information version 2.0 (www-.rubic.rdg.ac.uk).

B. Generation of the Human Anti-hGPAscFv-mRNK Fusion

A restriction fragment containing the scFv Bric-256 sequence described in 'A', above, is inserted into the plasmid described in Example 14 (in place of the sequence encoding Ter119 scFv). The remaining techniques of Example 14 are described.

C. hGPAscFv-mRNK is prepared as described in 'B', above. mRNK is radiolabeled with $^{125}$I—Na (Perkin Elmer, Wellesley, Mass.) using Iodogen (Pierce, Rockford, Ill.). Mouse and human red blood cells (mRBC and hRBC, suspended to 10% hematocrit) are loaded at the same concentration with hGPA-mRNK by incubation for one hour at 37° C. Unbound ligand is removed via centrifugation with PBS-BSA (phosphate buffered saline-bovine serum albumin) and RBC-bound radioactivity is measured in a γ-counter (Perkin Elmer).

Specific binding to hRBC is revealed vs. mRBC.

All documents listed in this specification are incorporated herein by reference. While the invention has been described with reference to specific embodiments, it will be appreciated that modifications can be made without departing from the spirit of the invention. Such modifications are intended to fall within the scope of the appended claims.

What is claimed is:

1. A fusion protein comprising a single chain antigen-binding domain (scFv) linked to thrombomodulin or a domain thereof, wherein said scFv binds to glycophorin A expressed on the surface of a red blood cell.

2. A fusion protein comprising a scFv linked to thrombomodulin or a domain thereof, wherein said scFv binds to glycophorin A on the surface of a red blood cell, and wherein at least 10% of the fusion protein injected into the bloodstream is maintained on the surface of said red blood cell in vivo for at least 48 hours.

3. The fusion protein according to claim 2, wherein at least 70% of the fusion protein injected into the bloodstream is maintained on the surface of a red blood cell in vivo for at least 48 hours.

4. A pharmaceutical composition comprising the fusion protein of claim 1 and a pharmaceutically acceptable carrier.

5. A method of delivering thrombomodulin or a domain thereof to the surface of a red blood cell comprising delivering a fusion protein according to claim 1 to a blood vessel.

6. A method of treating thrombosis, tissue ischemia, acute myocardial infarction (AMI), non-segmented elevated AMI, deep vein thrombosis, ischemic stroke, hyperoxic injury, transient ischemic attack (TIA), cerebrovascular disease, disseminated intravascular coagulation (DIC), pulmonary embolism, ischemic peripheral vascular disease, inflammation, pulmonary edema, sepsis, acute lung injury (ALI), acute respiratory distress syndrome (ARDS), and aseptic systemic inflammation, comprising administering a fusion protein according to claim 1 to a blood vessel in a mammal in need thereof.

* * * * *